(12) United States Patent
Koyama et al.

(10) Patent No.: US 12,036,103 B2
(45) Date of Patent: Jul. 16, 2024

(54) DISPOSABLE DIAPER

(71) Applicant: KAO CORPORATION, Tokyo (JP)

(72) Inventors: Izumi Koyama, Tokyo (JP); Hiroko Kawaguchi, Oyama (JP)

(73) Assignee: KAO CORPORATION, Tokyo (JP)

(*) Notice: Subject to any disclaimer, the term of this patent is extended or adjusted under 35 U.S.C. 154(b) by 1063 days.

(21) Appl. No.: 16/956,259

(22) PCT Filed: Dec. 22, 2017

(86) PCT No.: PCT/JP2017/046258
§ 371 (c)(1),
(2) Date: Jun. 19, 2020

(87) PCT Pub. No.: WO2019/123663
PCT Pub. Date: Jun. 27, 2019

(65) Prior Publication Data
US 2021/0077318 A1 Mar. 18, 2021

(51) Int. Cl.
*A61F 13/494* (2006.01)
(52) U.S. Cl.
CPC .................. *A61F 13/494* (2013.01)
(58) Field of Classification Search
CPC ............ A61F 13/494; A61F 2013/4944; A61F 2013/49493; A61F 2013/49025; A61F 2013/49028; A61F 2013/49026
See application file for complete search history.

(56) References Cited

U.S. PATENT DOCUMENTS 6,569,140 B1* 5/2003 Mizutani ............. A61F 13/4753
604/385.24
7,462,174 B2* 12/2008 Nishitani ............ A61F 13/5616
604/385.27
(Continued)

FOREIGN PATENT DOCUMENTS

CN 105455962 A 4/2016
EP 3357465 A1 8/2018
(Continued)

OTHER PUBLICATIONS

International Search Report, issued in PCT/JP2017/046258, PCT/ISA/210, dated Mar. 13, 2018.
(Continued)

*Primary Examiner* — Michele Kidwell
(74) *Attorney, Agent, or Firm* — Birch, Stewart, Kolasch & Birch, LLP

(57) ABSTRACT

Disclosed is a disposable diaper including a pair of leak-proof cuffs (6) provided respectively to both lateral sides of an absorbent assembly (5) along the longitudinal direction. Each leak-proof cuff (6) includes: an inwardly-oriented portion (63) wherein a leak-proof-cuff-forming sheet material (61) is arranged from a lateral side edge (43) of an absorbent core toward the absorbent member's inner side in the width direction; a fold-back portion (64) where the sheet material (61) is folded back toward the absorbent member's outer side in the width direction, the fold-back portion being located above the absorbent member (4); and an outwardly-folded portion (65) ranging from the fold-back portion (64) to a free end (6b) of the leak-proof cuff. The outwardly-folded portion (65) has a length, in the width direction, that is longer than the length of the inwardly-oriented portion (63), and a plurality of elastic members (62) are fixed in a stretched state to the outwardly-folded portion. The free end (6b) is located outside of the lateral side edge (43) of the
(Continued)

absorbent core. In the outwardly-folded portion (65), in a case where an elastic region (E) where the elastic members (62) are provided is divided, in the width direction, into two equal parts defined respectively as an inner region (E1) and an outer region (E2), the inner region (E1) has a higher elongation stress at 70% elongation than the outer region (E2).

20 Claims, 12 Drawing Sheets

(56) References Cited

U.S. PATENT DOCUMENTS

| | | | |
|---|---|---|---|
| 7,879,017 | B1 | 2/2011 | Tabata et al. |
| 10,092,460 | B2 * | 10/2018 | Takahashi ............ A61F 13/4942 |
| 11,318,053 | B2 * | 5/2022 | Mukai ................... A61F 13/494 |
| 2002/0045875 | A1 | 4/2002 | Minato et al. |
| 2002/0065502 | A1 * | 5/2002 | Shimizu ............ A61F 13/49413 604/385.24 |
| 2004/0059311 | A1 | 3/2004 | Minato et al. |
| 2004/0133180 | A1 * | 7/2004 | Mori ................. A61F 13/15804 604/385.25 |
| 2005/0107764 | A1 | 5/2005 | Matsuda et al. |
| 2005/0131375 | A1 * | 6/2005 | Sasaki ................... A61F 13/496 604/385.28 |
| 2010/0057036 | A1 | 3/2010 | Sperl et al. |
| 2010/0305532 | A1 | 12/2010 | Ashton et al. |
| 2014/0183510 | A1 | 6/2014 | Sperl et al. |
| 2015/0216734 | A1 | 8/2015 | Umemoto |
| 2017/0266065 | A1 | 9/2017 | Ashton et al. |
| 2017/0290714 | A1 | 10/2017 | Norimoto |
| 2020/0289340 | A1 * | 9/2020 | Arita ................... A61F 13/4752 |

FOREIGN PATENT DOCUMENTS

| | | |
|---|---|---|
| EP | 3 381 424 A1 | 10/2018 |
| JP | 10-90403 A | 4/1998 |
| JP | 11-188057 A | 7/1999 |
| JP | 11-285511 A | 10/1999 |
| JP | 11-347063 A | 12/1999 |
| JP | 2001-293031 A | 10/2001 |
| JP | 2006-332 A | 1/2006 |
| JP | 2006-81651 A | 3/2006 |
| JP | 2007-511326 A | 5/2007 |
| JP | 2008-93224 A | 4/2008 |
| JP | 2011-523887 A | 8/2011 |
| JP | 2012-100694 A | 5/2012 |
| JP | 2013-244255 A | 12/2013 |
| JP | 6037660 B2 | 12/2016 |
| JP | 2017-113347 A | 6/2017 |
| RU | 2 498 791 C2 | 11/2013 |
| WO | WO96/09025 A1 | 3/1996 |
| WO | WO96/19166 A1 | 6/1996 |
| WO | 2013/180117 * 12/2013 | ............ A61F 13/15 |
| WO | WO2017/130424 A1 | 8/2017 |
| WO | 2017/199300 * 11/2017 | ........... A61F 13/505 |
| WO | WO2017/199932 A1 | 11/2017 |

OTHER PUBLICATIONS

Extended European Search Report for European Application No. 17935633.2, dated Jun. 7, 2021.

* cited by examiner

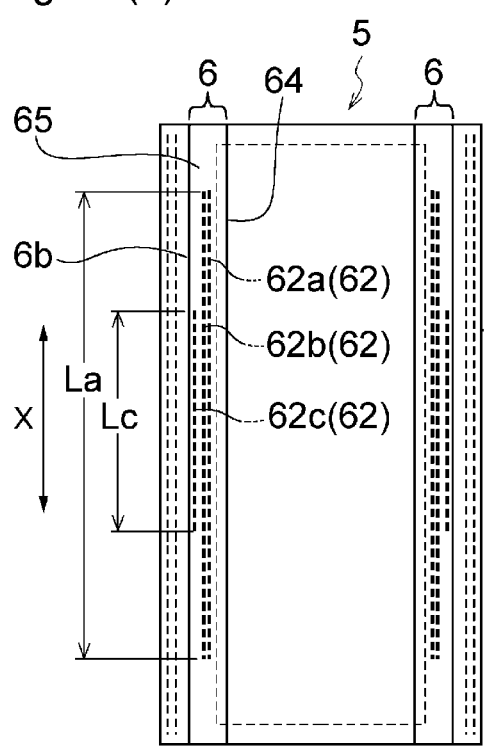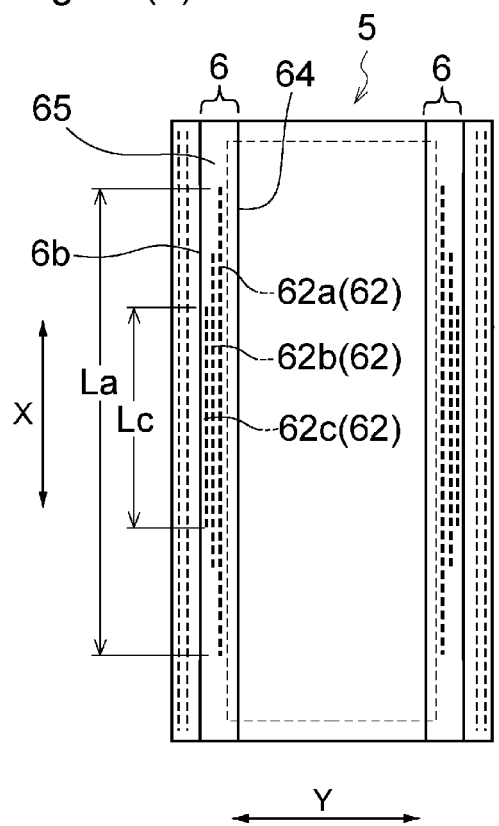

DISPOSABLE DIAPER

TECHNICAL FIELD

The present invention relates to a disposable diaper.

BACKGROUND ART

A disposable diaper known in the art includes an absorbent assembly including a topsheet, a backsheet and an absorbent member interposed between the topsheet and the backsheet, and also includes a pair of leak-proof cuffs that stands up toward the wearer's skin side, the leak-proof cuffs being provided respectively to the absorbent assembly's both lateral sides along the longitudinal direction. In many cases, the leak-proof cuffs are fixed at the absorbent assembly's both end portions in the longitudinal direction so as not to stand up. A known fixing technique is to fix, onto the topsheet on the absorbent member, a section of the leak-proof cuff that is arranged from the outer side, in the absorbent assembly's width direction, toward the inner side, and also join a section folded back toward the outer side in the width direction onto a lower member that is located on the lower surface side of that section (see Patent Literature 1).

Patent Literature 2 discloses an absorbent article such as a sanitary napkin, wherein a section of a leak-proof cuff that is folded back toward the outer side in the absorbent article's width direction includes: a section that is fixed to the topsheet side; and a section that projects out from the aforementioned section and is not joined to any other member.

In general, when a wearer puts on a pull-on disposable diaper having a waist opening and a pair of leg openings formed in advance, the wearer passes his/her legs one by one through the leg openings, and then pulls the diaper up to the wearer's hips.

In conventional disposable diapers with leak-proof cuffs, however, the wearer's foot may get caught on the leak-proof cuff when passing his/her foot/leg through the leg opening. This may result in the leak-proof cuffs not contacting the wearer's skin in a proper state when the diaper is worn, thereby not being able to achieve a good leakage preventive effect by the leak-proof cuffs. Also, in order to make the leak-proof cuffs contact the wearer's skin properly, the position/orientation of the leak-proof cuffs may need to be adjusted by inserting the fingers through the leg openings after pulling the diaper up to the hips. Such a need, however, may be a burden on users, such as a parent of a baby/toddler, a caregiver, or a wearer putting on the diaper by himself/herself.

CITATION LIST

Patent Literature

Patent Literature 1: JP H11-285511A
Patent Literature 2: JP 2013-244255A

SUMMARY OF INVENTION

The present invention relates to a disposable diaper having a longitudinal direction along a front-rear direction of a wearer and a width direction orthogonal to the longitudinal direction, the disposable diaper including a rear portion to be arranged on the wearer's rear side when worn, a front portion to be arranged on the wearer's front side and a crotch portion located between the rear portion and the front portion.

The disposable diaper includes: an absorbent assembly including a topsheet, a backsheet and an absorbent member that is interposed between the topsheet and the backsheet and that includes an absorbent core; and a pair of leak-proof cuffs provided respectively to the absorbent assembly's both lateral sides along the longitudinal direction.

Each of the leak-proof cuffs includes a leak-proof-cuff-forming sheet material and elastic members fixed to the sheet material, and includes: an inwardly-oriented portion wherein the sheet material is arranged from a lateral side edge of the absorbent core toward the absorbent member's inner side in the width direction; a fold-back portion where the sheet material is folded back toward the absorbent member's outer side in the width direction, the fold-back portion being located above the absorbent member; and an outwardly-folded portion ranging from the fold-back portion to a free end of the leak-proof cuff.

The outwardly-folded portion has a length, in the width direction, that is longer than the length of the inwardly-oriented portion; and the plurality of elastic members are fixed in a stretched state to the outwardly-folded portion along the longitudinal direction. The free end of the leak-proof cuff is located widthwisely outside of the lateral side edge of the absorbent core.

In the outwardly-folded portion, in a case where a region where the plurality of elastic members are provided is divided, in the outwardly-folded portion's width direction, into two equal parts defined respectively as an inner region and an outer region, the inner region has a higher elongation stress at 70% elongation than the outer region.

BRIEF DESCRIPTION OF DRAWINGS

FIGS. 10(a) and 10(b) are plan views of absorbent assemblies illustrating preferred examples of the length of extensible ranges of elastic members provided to the first leakproof cuff.

FIGS. 11(a) to 11(c) are diagrams illustrating an example of an arrangement of joined portions that join the outwardly-folded portion and inwardly-oriented portion of the disposable diaper illustrated in FIG. 1 to respective lower members which are located on the lower surface side of the respective portions.

DESCRIPTION OF EMBODIMENTS

The present invention provides a disposable diaper capable of overcoming the drawbacks of the aforementioned conventional art.

Preferred embodiments of a disposable diaper of the present invention are described below with reference to the drawings.

Figure 1:
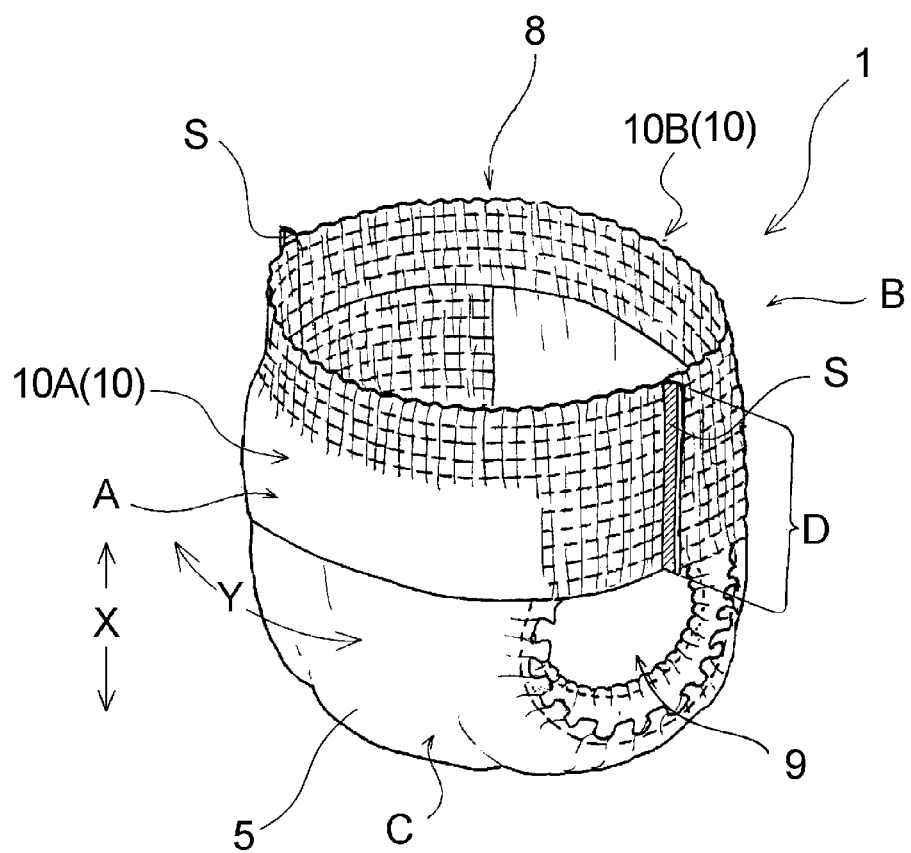
FIG. 1 is a perspective view illustrating a disposable diaper according to an embodiment of the present invention.

A disposable diaper 1 according to an embodiment of the present invention is described with reference to FIGS. 1 to 3. As illustrated in FIG. 1, the disposable diaper 1 of the present embodiment (referred to hereinafter also as "diaper 1") is a pull-on disposable diaper, and includes an absorbent assembly 5 including a topsheet 2, a backsheet 3 and an absorbent member 4 that is interposed between the two sheets 2, 3. The diaper 1 also includes an outer cover 10 fixed to the absorbent assembly 5. The diaper 1 also includes a front portion A to be arranged on the wearer's front side when worn, a crotch portion C to be arranged at the wearer's crotch section, and a rear portion B to be arranged on the rear side. Both end portions in the front portion A in the width direction Y are joined respectively with both end portions in the rear portion B in the width direction Y, thereby forming a pair of side seals S, S. This joining also forms a waist opening 8 and a pair of leg openings 9 (although only one is illustrated in the figure).

The diaper 1 of the present embodiment is a pull-on disposable diaper wherein the outer cover 10 is divided into the front portion A side and the rear portion B side. The diaper 1 includes a front panel 10A to be arranged on the wearer's front side, a rear panel 10B to be arranged on the wearer's rear side, and the absorbent assembly 5 fixed in a manner bridging the front panel 10A and the rear panel 10B. The front panel 10A and the rear panel 10B are joined together at the pair of side seals S, S. As illustrated in FIG. 2, the absorbent assembly 5 is fixed in a manner bridging the central portion, in the width direction Y, of the front panel 10A located in the front portion A and the central portion, in the width direction Y, of the rear panel 10B located in the rear portion B. The sections of the absorbent assembly 5 respectively overlapping the front panel 10A and the rear panel 10B are joined respectively to the panels 10A, 10B either partially or over the entire surface by a known joining means such as an adhesive. At both ends, in the width direction Y, of the front and/or rear panels, the outer cover 10 may include a narrow-width region—e.g., a region that is 10 mm or less—where the front panel 10A and the rear panel 10B are not joined together. Such a configuration is also encompassed within cases where the front portion A and the rear portion B are joined together at both end portions in the width direction Y.

Figure 2:
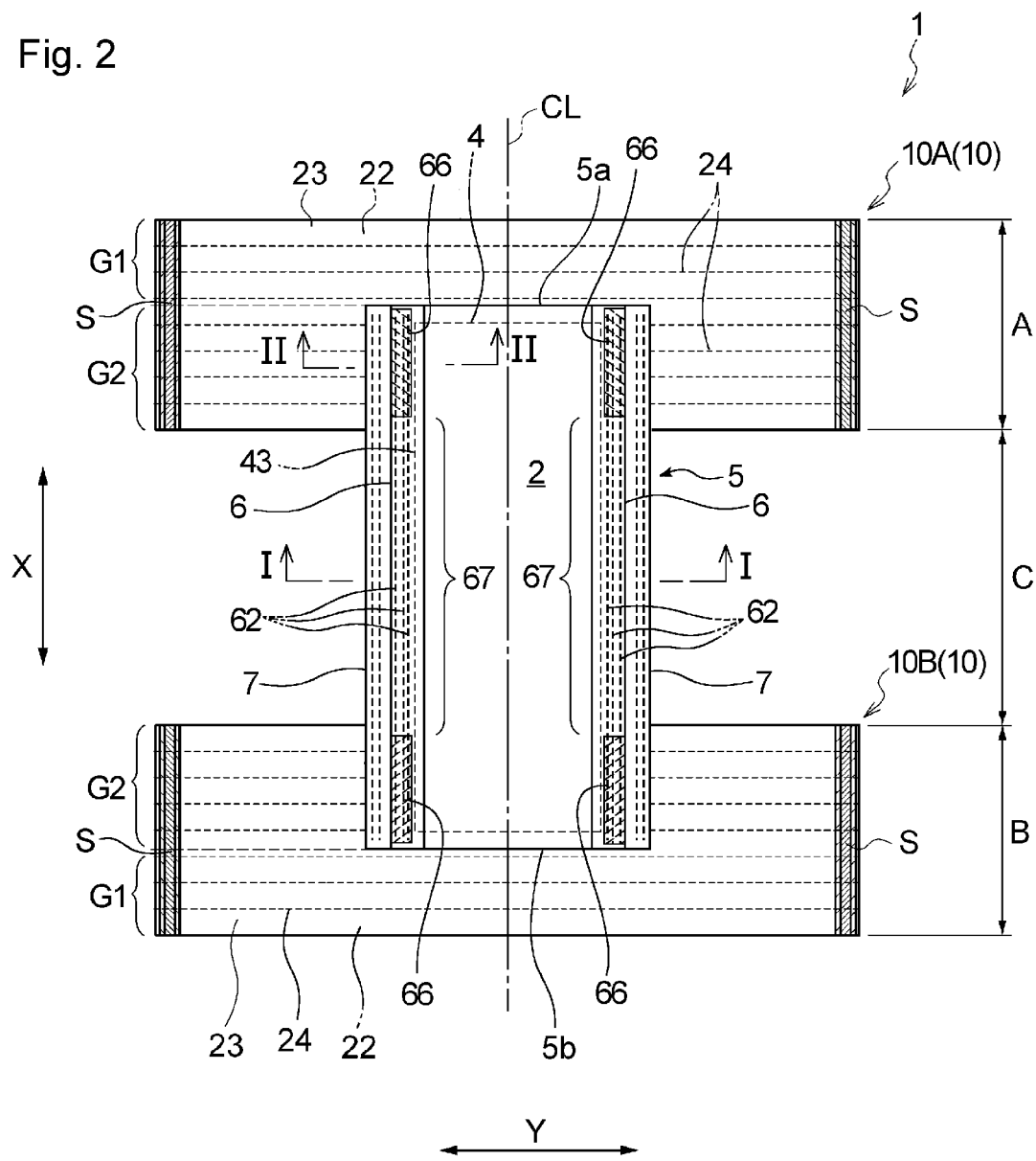
FIG. 2 is a plan view, as viewed from the skin-facing surface side, of the disposable diaper illustrated in FIG. 1 in its spread-open and stretched state, wherein the spread-open and stretched state of a pull-on disposable diaper refers to a state in which the side seals are torn apart to bring the disposable diaper in a spread-out (developed) state, and the elastic members in various parts of the spread-out diaper are stretched so that the diaper is spread to its designed size (size when the diaper is spread out in a planar manner in a state where the effect of the elastic members is completely eliminated).

As illustrated in FIG. 2, the diaper 1 of the present embodiment is formed so as to have left-right symmetry with respect to a longitudinal center line CL extending along the diaper 1's longitudinal direction X. Therefore, in the description below, for parts having left-right symmetry, only the parts on the left-hand side in FIG. 2 will mainly be explained, but the features on the right-hand side have the same configuration, except that they are symmetrical to the parts on the left-hand side.

The diaper 1 includes a crotch portion C located in the central region in the longitudinal direction X, and a front portion A and a rear portion B that respectively extend frontward and rearward from the crotch portion C in the longitudinal direction X. The diaper 1's longitudinal direction X is the direction along the front-rear direction of a wearer when the diaper is worn. More specifically, the diaper's longitudinal direction is the direction extending from the section to be arranged on the wearer's front side to the section to be arranged on the rear side via the section to be arranged at the crotch, and matches the longitudinal direction of the absorbent assembly 5 and the longitudinal direction of the absorbent member 4. On the other hand, the width direction Y is the direction orthogonal to the longitudinal direction X in a state where the absorbent article, such as the diaper, is spread open and the various elastic members are stretched, as illustrated in FIG. 2. The width direction also matches the circumferential direction of the tubular below-waist portion D formed by connecting the front portion A and the rear portion B, as illustrated in FIG. 1.

In the present Description, the "skin-facing surface" or "upper surface" refers to the surface, among the front and back surfaces of the disposable diaper or the constituent members thereof, that is to be arranged on the wearer's skin side when the diaper is worn. The "non-skin-facing surface" or "lower surface" refers to the surface, among the front and back surfaces of the disposable diaper or the constituent members thereof, that faces the opposite side from the wearer's skin side when the diaper is worn. Note that, in relation to the various members—such as the inwardly-oriented portion 63, fold-back portion 64, outwardly-folded portion 65, lateral extension portion 68, etc.—of the later-described leak-proof cuffs, the "lower surface" refers to the surface on the backsheet 3 side of the disposable diaper in its spread-open and stretched state, and is the surface facing the lower side in FIGS. 3 and 4.

As illustrated in FIG. 2, in the diaper 1 of the present embodiment, each of the front panel 10A and the rear panel 10B constituting the outer cover 10 includes: an outer sheet 22 constituting the diaper's outer surface; an inner sheet 23 provided on the inner surface side of the outer sheet 22; and a plurality of thread-shaped elastic members 24 arranged in a stretched state between the sheets 22, 23. Each of the front and rear panels includes a waist elasticized portion G1 and a below-waist elasticized portion G2. The waist elasticized portion G1 is formed on the outer side, in the diaper 1's longitudinal direction X, of the absorbent assembly 5's respective ends 5a, 5b in the longitudinal direction. The waist elasticized portion G1 is formed in the peripheral edge portion of the waist opening 8, and is to be arranged in the wearer's waist portion when the diaper is worn. The below-waist elasticized portion G2 is formed in each of the front panel 10A and the rear panel 10B in a region below the waist elasticized portion G1 and above the lower end of the side seals S. In the waist elasticized portion G1 and the below-waist elasticized portion G2, the outer sheet 22 and the inner sheet 23 may be joined together over the entire region, or be joined by a plurality of joined portions formed with intervals therebetween in the longitudinal direction X and the width direction Y.

As illustrated in FIG. 2, the absorbent member 4 of the diaper 1 is formed in a shape that is long in the same direction as the diaper 1's longitudinal direction. The absorbent member 4 includes: an absorbent core 41 constituted by an aggregate of fibers, such as pulp fibers, or a fiber aggregate retaining water-absorbent polymer particles; and a core-wrap sheet 42 covering the absorbent core 41. The fiber aggregate may be made by accumulating pulp fibers etc. in a predetermined shape, or may be a nonwoven fabric. The topsheet 2 covers the entire region of the skin-facing surface of the absorbent member 4. The backsheet 3 covers the entire region of the non-skin-facing surface of the absorbent member 4. Further, on the non-skin-facing surface side of the absorbent assembly 5—i.e., the non-skin-facing surface side of the backsheet 3—in the crotch portion C, an outer nonwoven fabric 32 that covers the non-skin-facing surface is provided from the viewpoint of improving texture to the touch.

Figure 3:
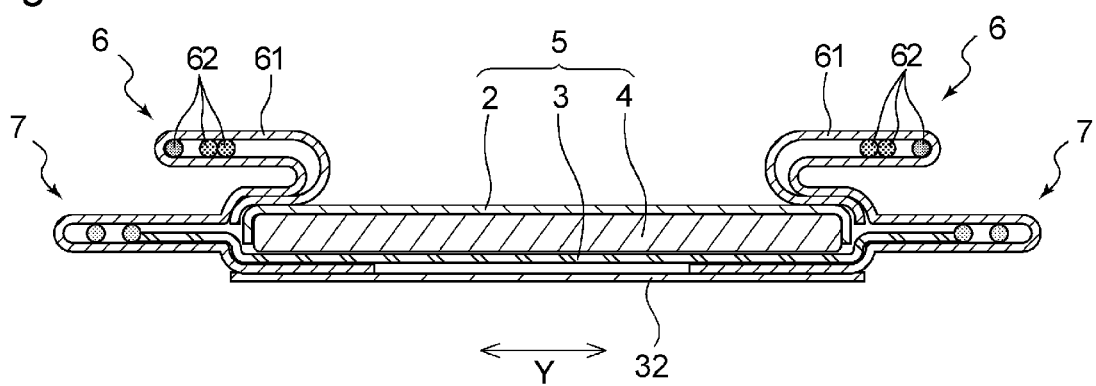
FIG. 3 is a cross-sectional view taken along line I-I of FIG. 2.

As illustrated in FIG. 3, the absorbent assembly 5 includes, on the respective lateral sides along the longitudinal direction X: a pair of first leak-proof cuffs 6 serving as "leak-proof cuffs" in the present invention; and second leak-proof cuffs 7 formed widthwisely outside of the respective first leak-proof cuffs 6. The first leak-proof cuffs 6 and the second leak-proof cuffs 7 are arranged along the longitudinal direction of the absorbent assembly 5.

Figure 4:
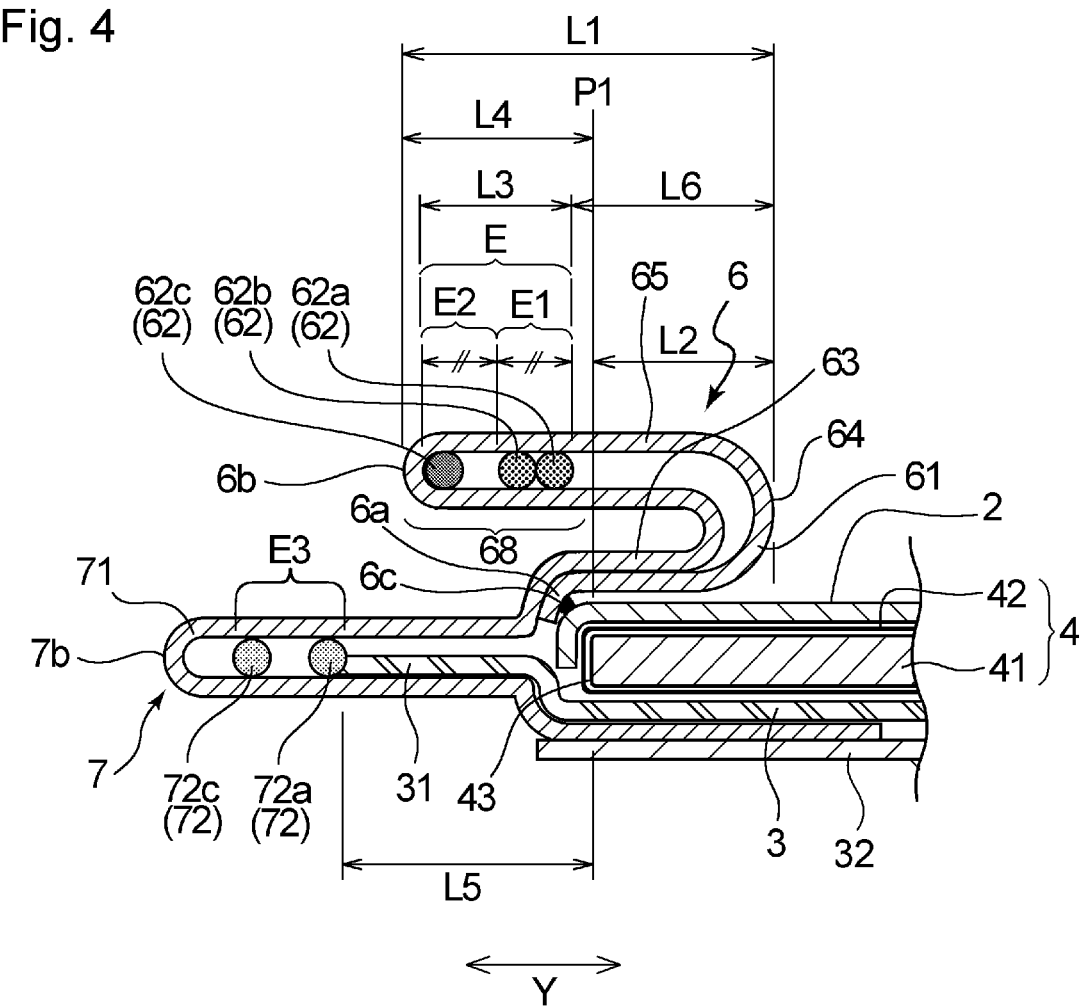
FIG. 4 is an enlarged view of first and second leak-proof cuffs on the left-hand side in FIG. 3.

As illustrated in FIG. 4, the first leak-proof cuff 6 includes: a first leak-proof-cuff-forming sheet material 61; and a plurality of first leak-proof-cuff-forming elastic members 62 fixed to the sheet material 61. The sheet material 61 in the diaper 1 of the present embodiment is a multilayer-structure laminate sheet including a two-layer structure formed by folding a single sheet in two along a folding/bending portion formed at the free end of the first leak-proof cuff 6. The elastic members 62 are fixed by an adhesive between the layers of the laminate sheet. Examples of methods for fixing the elastic members 62 to the sheet material 61 may include: a method of sandwiching the elastic members 62 between sheets to which an adhesive has been applied to one or both of the opposing surfaces; and a method of applying an adhesive to the elastic members 62 and fixing the elastic members 62 with the adhesive to the sheet material 61 substantially only at the sections where the elastic members 62 are arranged. The same applies to the method for fixing the elastic members to the later-described second leak-proof-cuff-forming sheet material 71.

As illustrated in FIG. 4, the second leak-proof cuff 7 includes: a second leak-proof-cuff-forming sheet material 71; and second elastic members 72 for forming the second leak-proof cuff that are fixed to the sheet material 71. The sheet material 71 in the diaper 1 of the present embodiment is a multilayer-structure laminate sheet including a two-layer structure formed by folding a single sheet in two along a folding/bending portion formed at the tip end 7b, in the extending direction, of the second leak-proof cuff 7. The second elastic members 72 are fixed by an adhesive between the layers of the laminate sheet. The laminate sheet constituting the second leak-proof cuff 7's absorbent member side, which is the base portion side in the extending direction, has a three-layer structure wherein an extension portion of the backsheet 3 is interposed between the two layers of the nonwoven fabric sheet.

As illustrated in FIG. 4, in the vicinity of the absorbent member 4's lateral side along the longitudinal direction, the first leak-proof cuff 6 includes a fixed end 6a that is fixed to the topsheet 2. More specifically, in the vicinity of the absorbent core 41's lateral side edge 43 along the longitudinal direction, the first leak-proof-cuff-forming sheet material 61 includes a linear joined portion 6c that is fixed to the topsheet 2, and the linear joined portion 6c's end portion on the inner side in the width direction constitutes the fixed end 6a of the first leak-proof cuff 6. The linear joined portion 6c is preferably formed as a continuous straight line extending along the longitudinal direction X, but may be formed as a dotted line. As for the joining method for forming the linear joined portion 6c, any discretionary joining method can be employed, such as heat-sealing, ultrasonic sealing, high-frequency sealing, or joining with an adhesive; two or more joining methods may be employed in combination.

Figure 6:
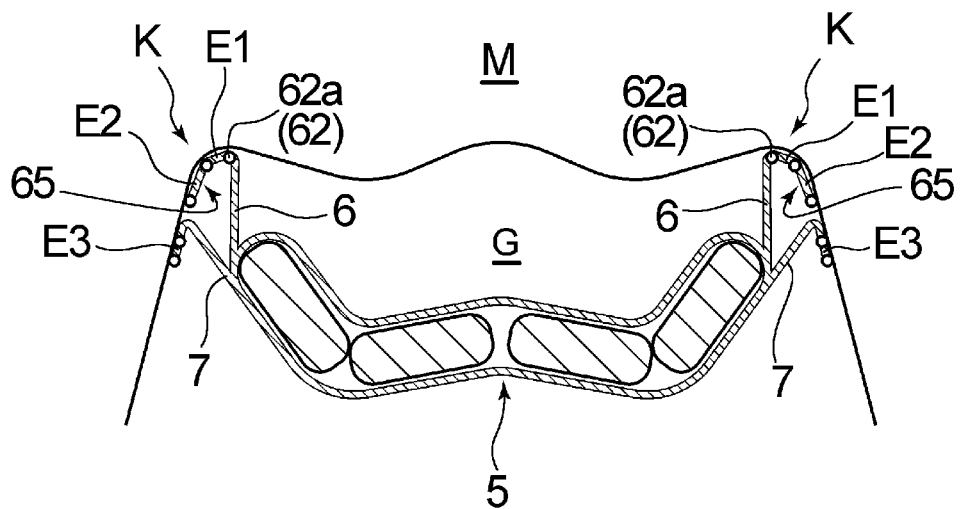
FIG. 6 is a schematic widthwise cross-sectional view of a central section of a crotch portion when the disposable diaper of FIG. 1 is worn.

As illustrated in FIG. 6, at least a section of the first leak-proof cuff 6 located in the crotch portion C's central section in the longitudinal direction stands up toward the wearer M's skin side when the diaper is worn, and a region where the elastic member 62 is provided—preferably a continuous elastic region E where the plurality of elastic members 62 are provided—comes into contact with the vicinity of the wearer M's inguinal region K. Further, at least the section of the second leak-proof cuff 7 located in the crotch portion C's central section in the longitudinal direction extends toward the wearer M's skin side when the diaper is worn, and an elastic region E3 where the second elastic member 72 is provided—preferably a continuous region E3 where the plurality of elastic members 72 are provided—comes into contact with a section of the wearer M's inner femoral region that is located closer to the knee than the contact point of the first leak-proof cuff 6.

As illustrated in FIG. 2, in the vicinity of the absorbent assembly 5's both end portions in the longitudinal direction which are located respectively in the front portion A and the rear portion B, the first leak-proof cuff 6 also includes an end-portion fixed region 66 in which the first leak-proof cuff 6 is fixed so as not to stand up.

Figure 5:
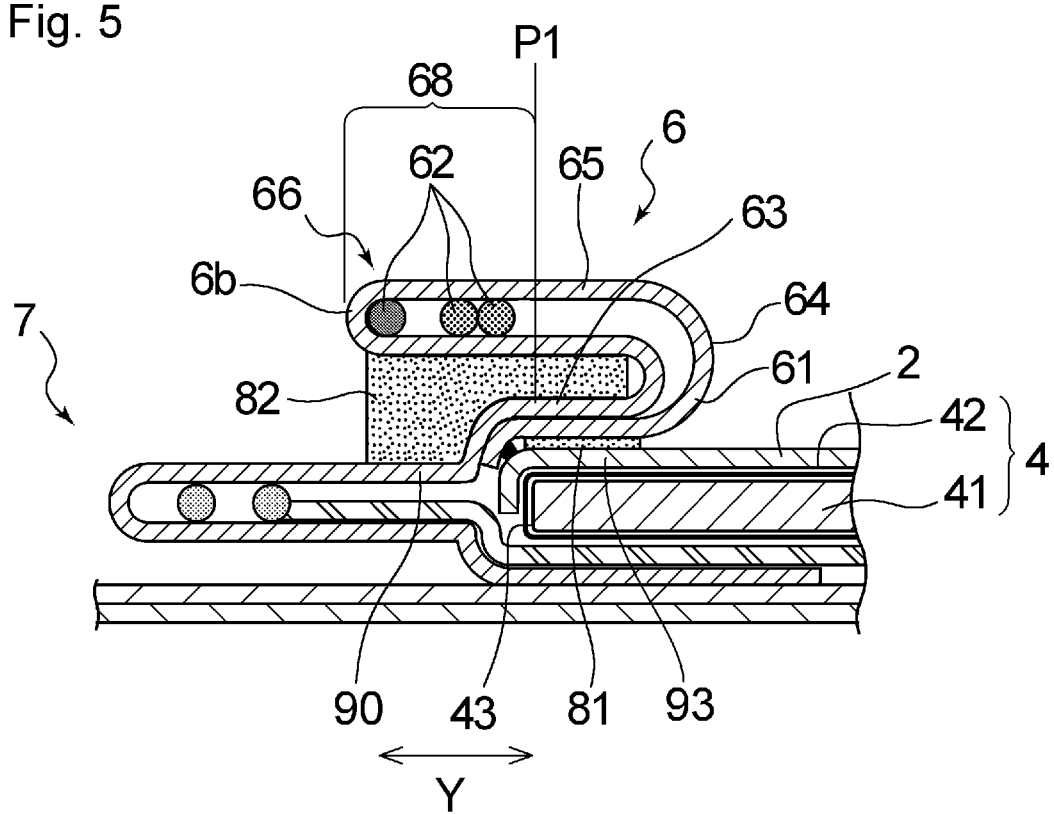
FIG. 5 is an enlarged cross-sectional view taken along line II-II of FIG. 2.

In both of the end-portion fixed region 66 formed in the front portion A and the end-portion fixed region 66 formed in the rear portion B, each first leak-proof cuff 6 includes, as illustrated in FIG. 5: an inwardly-oriented portion 63 wherein the first leak-proof-cuff-forming sheet material 61 is arranged from the lateral side edge 43 of the absorbent core 41 toward the absorbent member 4's inner side in the width direction Y; a fold-back portion 64 where the first leak-proof-cuff-forming sheet material 61 is folded back from the inwardly-oriented portion 63 toward the absorbent member 4's outer side in the width direction Y, the fold-back portion 64 being located above the absorbent member 4; and an outwardly-folded portion 65 ranging from the fold-back portion 64 to the free end 6b of the first leak-proof cuff 6. In the first leak-proof cuff 6 within the end-portion fixed region 66, the inwardly-oriented portion 63 is fixed by a known joining means 81 such as an adhesive onto the topsheet 2, which covers the absorbent member 4's skin-facing surface side, in a laid-down state toward the absorbent assembly 5's inner side in the width direction; whereas the outwardly-folded portion 65, which ranges from the fold-back portion 64 to the free end 6b, is fixed by a known joining means 82 such as an adhesive to a lower member 90, which is located on the outwardly-folded portion's lower surface side, in a laid-down state toward the absorbent assembly 5's outer side in the width direction. Herein, the "lower member 90 located on the lower surface side" refers to a member opposing the outwardly-folded portion 65's non-skin-facing surface in a disposable diaper in a spread-open and stretched state; in the diaper 1 of the present embodiment, the lower member 90 corresponds to the first leak-proof cuff 6's inwardly-oriented portion 63 and the second leak-proof cuff 7, and more specifically, corresponds to sections opposing the outwardly-folded portion 65's non-skin-facing surface in each of the first leak-proof-cuff-forming sheet material 61 and the second leak-proof-cuff-forming sheet material 71. For the joining means 81, 82, any discretionary joining method can be employed, such as heat-sealing, ultrasonic sealing, high-frequency sealing, or joining with an adhesive; two or more joining methods may be employed in combination.

The first leak-proof cuff 6 is fixed in a folded/bent state in the cross-sectional shape as illustrated in FIG. 5 within each end-portion fixed region 66 located in the front portion A and the rear portion B. Thus, also in a non-fixed region 67 located between both end-portion fixed regions 66 in the longitudinal direction X of the absorbent assembly 5, as illustrated in FIG. 4, the first leak-proof cuff 6 of the diaper 1 in a spread-open and stretched state (see FIG. 2) is folded/bent in the same cross-sectional shape as the cross-sectional shape within the end-portion fixed region 66, and thus includes: an inwardly-oriented portion 63 wherein the first leak-proof-cuff-forming sheet material 61 is arranged from the lateral side edge 43 of the absorbent core 41 toward the absorbent member 4's inner side in the width direction Y; a fold-back portion 64 where the first leak-proof-cuff-forming sheet material 61 is folded back toward the absorbent member 4's outer side in the width direction Y, the fold-back portion 64 being located above the absorbent member 4; and an outwardly-folded portion 65 ranging from the fold-back portion 64 to the free end 6b of the first leak-proof cuff 6. Note that, in the longitudinal direction of the first leak-proof cuff 6 of the diaper 1 in a spread-open and stretched state, the fold-back portion 64 is preferably located on/above the absorbent member 4—and more preferably located widthwisely inside of (more toward the center line CL side, in the width direction Y, than) the lateral side edge 43 of the absorbent core 41—at least in sections where the respective end-portion fixed regions 66 on the front portion A side and the rear portion B side are provided. Further, in the longitudinal direction of the first leak-proof cuff 6 of the diaper 1 in a spread-open and stretched state, the fold-back portion 64 is preferably located on/above the absorbent member 4—and more preferably located widthwisely inside of (more toward the center line CL side, in the width direction Y, than) the lateral side edge 43 of the absorbent core 41—in a portion or the entire region, in the longitudinal direction, of the non-fixed region 67 located between the end-portion fixed regions 66.

Further, in the diaper 1 in a spread-open and stretched state (see FIG. 2), as illustrated in FIG. 4, the first leak-proof cuff 6 has the following configurations 1 to 3.

Configuration 1: The outwardly-folded portion 65 has a length, in the width direction Y, that is longer than the length of the inwardly-oriented portion 63. More specifically, the distance from the fold-back portion 64 to the first leak-proof cuff 6's free end 6b—i.e., the outwardly-folded portion 65's length L1 in the width direction, which is the length measured along the width direction Y of the absorbent assembly 5—is longer than the distance from the position of the absorbent core 41's lateral side edge 43 to the inner end of the fold-back portion 64—i.e., the inwardly-oriented portion 63's length L2 in the width direction, which is the length measured along the width direction Y of the absorbent assembly 5.

Configuration 2: A plurality of elastic members 62 are each fixed in a stretched state to the outwardly-folded portion 65 along the longitudinal direction X. More specifically, a plurality of elastic members 62 are arranged in an extensible manner along the longitudinal direction of the first leak-proof cuff 6 within a range from the fold-back portion 64 to the first leak-proof cuff 6's free end 6b. FIG. 4 illustrates an example in which three elastic members 62 are provided to the outwardly-folded portion 65, but the number of elastic members 62 is not limited to three. From the viewpoint of improving leakage preventability by causing a wide area of the first leak-proof cuff 6 in the width direction to contact the wearer's skin, it is preferable that the number of elastic members 62 provided to the outwardly-folded portion 65 is preferably two or greater, more preferably three or greater; also, from the viewpoint of preventing the wearer's foot from getting caught on the leak-proof cuff when passing the leg/foot through the leg opening due to the leak-proof cuff being too wide in the width direction, the number of elastic members is preferably ten or fewer, more preferably five or fewer, and preferably from two to ten, more preferably from three to five.

Configuration 3: In the first leak-proof cuff 6, the free end 6b of the first leak-proof cuff 6 is located widthwisely outside of the lateral side edge 43 of the absorbent core 41. More specifically, the first leak-proof cuff 6 includes a lateral extension portion 68 that extends more toward the outer side, in the width direction Y, than the lateral side edge 43 of the absorbent core 41. It is preferable that the lateral extension portion 68 is provided with at least one elastic member 62, more preferably with a plurality of elastic members.

Further, in the outwardly-folded portion 65 of the first leak-proof cuff 6 in the diaper 1 of the present embodiment, in a case where a region E where the plurality of elastic members 62a to 62c are provided is divided, in the outwardly-folded portion 65's width direction Y, into two equal parts defined respectively as an inner region E1 and an outer region E2 as illustrated in FIG. 4, the inner region E1 has a higher elongation stress at 70% elongation than the outer region E2. The "region E where the plurality of elastic members are provided" is a region, in the outwardly-folded portion 65, from the inner end, in the width direction, of the elastic member 62a arranged most inward in the width direction Y to the outer end, in the width direction, of the elastic member 62c arranged most outward in the width direction Y. The region E where the plurality of elastic members are provided in the outwardly-folded portion 65 is also referred to simply as "elastic region E".

It is preferable that, in the disposable diaper of the invention, no elastic member for imparting extensibility in the longitudinal direction to the leak-proof cuff is provided to the leak-proof cuff's inwardly-oriented portion 63 and fold-back portion 64, and more preferably, no such elastic member is provided particularly to the inwardly-oriented portion 63. In the first leak-proof cuff 6 of the diaper 1 of the present embodiment, no elastic member is provided along the longitudinal direction in either the inwardly-oriented portion 63 or the fold-back portion 64.

According to the diaper 1 of the present embodiment, since the first leak-proof cuff 6 has the aforementioned configurations 1 to 3 in the diaper 1 in a spread-open and stretched state (see FIG. 2), it is possible to reduce in the width of the crotch portion C and also widen the width of a region capable of absorbing excreted fluid between the first leak-proof cuffs 6 in the crotch portion C (referred to hereinafter also as "hydrophilic width"). Also, when putting the diaper 1 on the wearer, the wearer's foot etc. is prevented from getting caught on the first leak-proof cuff 6 or the peripheral edge portion around the leg opening, thus allowing the diaper to be worn smoothly.

Since it is possible to achieve both reduction in the width of the crotch portion C and widening of the hydrophilic width, the wearer can move his/her legs easily during use, while attaining the effect of suppressing leakage.

Furthermore, the first leak-proof cuff 6 includes an elastic region E wherein the elongation stress at 70% elongation is higher in the inner region E1 than in the outer region E2. Thus, as illustrated in FIG. 6, the inner region E1—which is located on the inner side, in the width direction, of the outwardly-folded portion 65—can easily come into contact with the wearer's inguinal region K, whereas the outer region E2—which is located on the outer side in the width direction—can easily come into contact with and conform to the skin surface of the wearer M's inner femoral region. This allows a wide area, in the width direction, of the outwardly-folded portion 65 to easily contact the wearer's skin, thereby suppressing the formation of a gap between the first leak-proof cuff 6 and the wearer's skin. Thus, for example, a gap is less likely to be formed between the first leak-proof cuff 6 and the wearer's skin, even when the diaper 1 absorbs a large amount of excrement and thereby the force that lowers the diaper 1 is increased.

It is also possible to make the first leak-proof cuffs contact the wearer's skin surface properly as illustrated in FIG. 6, even without adjusting the position/orientation of the first leak-proof cuffs 6 by inserting the fingers through the leg openings after pulling the diaper up to the hips. Thus, at the time of putting on the diaper, it is possible to reduce the burden on users, such as a parent of a baby/toddler, a caregiver, or a wearer putting on the diaper by himself/herself.

The elongation stress at 70% elongation of each of the inner region E1 and the outer region E2 is measured as follows.

{Method for Measuring Elongation Stress at 70% Elongation of Inner Region E1 and Outer Region E2}

A sample of the outwardly-folded portion 65, whose length in the longitudinal direction X is equivalent to the entire length of the first leak-proof cuff 6 in the longitudinal direction X and whose length in the width direction Y is equivalent to the entire width of the outwardly-folded portion 65, is cut out from the first leak-proof cuff 6 of the disposable diaper in a spread-open and stretched state (FIG. 2). The sample is cut at the boundary between the inner region E1 and the outer region E2 (i.e., the boundary that divides the elastic region E into two equal parts in the width direction), to thereby obtain measurement samples respectively for the inner region E1 and the outer region E2. In cases where an elastic member is present at the boundary, both the pair of left and right first leak-proof cuffs are employed, and, from one first leak-proof cuff, a continuous measurement sample for the inner region E1 is obtained including the elastic member in the vicinity of one lateral side edge, and from the other first leak-proof cuff, a continuous measurement sample for the outer region E2 is obtained including the elastic member in the vicinity of one lateral side edge.

Figure 7A:
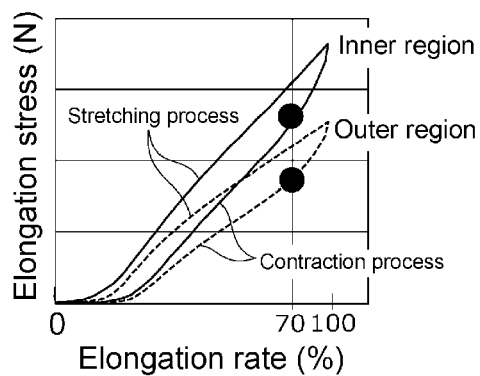
FIG. 7($a$) is an example of a S-S curve used for measuring the stress at 70% elongation of an inner region and an outer region of an outwardly-folded portion, and FIG. 7($b$) is an example of a S-S curve used for measuring the stress at 70% elongation of an elastic region of the second leak-proof cuff, shown together with the S-S curve of the outer region.

For each measurement sample for the respective inner region E1 and the outer region E2, the inner end portion (i.e., the end portion on the crotch portion C side closer to the center in the longitudinal direction X) of each end-portion fixed region 66 located at opposite ends in the longitudinal direction is pinched respectively by upper and lower chucks of a Tensilon tensile tester (Autograph AG-X 1 kN from Shimadzu Corporation), and a tensile test is performed wherein the region located between the end-portion fixed regions 66 in each measurement sample (referred to hereinafter also as "measurement target region") is stretched in the longitudinal direction of the first leak-proof cuff. More specifically, the measurement target region of the measurement sample is stretched at a rate of 300 m/minute until the chuck-to-chuck distance is expanded from the natural length Ls of the measurement target region to the length Lmax at the maximum stretched state (stretching process). Then, at the same rate, the chuck-to-chuck distance is reduced until it returns to the initial length, which is the same length as the natural length Ls of the measurement target region of the measurement sample (contraction process). A stress-strain curve (S-S curve) is created (see FIG. 7(a)), which is a graph illustrating the relationship between normal stress and normal strain during the processes. The stress at the point where the elongation rate in the contraction process is 70% is read from the curve, and this is considered the stress at 70% elongation.

In the measurement target region of the measurement sample, the "natural length Ls" is the length in a naturally contracted state without applying any external force except for gravity. The "maximum stretched state" is a state wherein the measurement target region (the region between the chucks) of each measurement sample is stretched out to the length of the measurement target region when the disposable diaper is in its spread-open and stretched state (i.e., to the length of the region located between the end-portion fixed regions 66). The "length Lmax at the maximum stretched state" is the same length as the length between the end-portion fixed regions 66 of the first leak-proof cuff when the disposable diaper is in its spread-open and stretched state. The "length Lmax at the maximum stretched state" is the same as the length of the measurement target region when the contractile force of the elastic members included in each measurement sample is eliminated by cutting, removal, etc., and only the sheet material is spread out in a planar manner. "Elongation rate of 70%" is the point, during the contraction process, when the elongation rate calculated by the following equation reaches 70%.

Elongation rate (%)=[($Le-Ls$)/($L$max$-Ls$)]×100.

(In the equation, Le is the chuck-to-chuck distance at a discretionary point, Ls is the initial length of the measurement target region, and Lmax is the length at the maximum stretched state of the measurement target region.)

From the viewpoint of achieving one or more of the aforementioned effects more reliably, it is preferable that the first leak-proof cuff 6 has the following configurations.

The outwardly-folded portion 65's length L1 in the width direction is preferably 1.1 times or greater, more preferably 1.5 times or greater, and preferably 5 times or less, more preferably 3 times or less, and preferably from 1.1 to 5 times, more preferably from 1.5 to 3 times, the inwardly-oriented portion 63's length L2 in the width direction.

The outwardly-folded portion 65's length L1 in the width direction is preferably 10 mm or greater, more preferably 15 mm or greater, and preferably 50 mm or less, more preferably 40 mm or less, and preferably from 10 to 50 mm, more preferably from 15 to 40 mm.

The inwardly-oriented portion 63's length L2 in the width direction is preferably 5 mm or greater, more preferably 8 mm or greater, and preferably 45 mm or less, more preferably 35 mm or less, and preferably from 5 to 45 mm, more preferably from 8 to 35 mm.

The elastic region E's length L3 in the width direction to the outwardly-folded portion 65's length L1 in the width direction is preferably 15% or greater, more preferably 30% or greater, and preferably 80% or less, more preferably 65% or less, and preferably from 15 to 80%, more preferably from 30 to 65%.

The elastic region E's length L3 in the width direction is preferably 3 mm or greater, more preferably 6 mm or greater, and preferably 25 mm or less, more preferably 20 mm or less, and preferably from 3 to 25 mm, more preferably from 6 to 20 mm.

The length L4, in the width direction, of the first leak-proof cuff 6's lateral extension portion 68 to the outwardly-folded portion 65's length L1 in the width direction is preferably 15% or greater, more preferably 35% or greater, and preferably 85% or less, more preferably 65% or less, and preferably from 15 to 85%, more preferably from 35 to 65%.

The lateral extension portion 68's length L4 in the width direction is preferably 3 mm or greater, more preferably 6 mm or greater, and preferably 30 mm or less, more preferably 25 mm or less, and preferably from 3 to 30 mm, more preferably from 6 to 25 mm.

The elongation stress at 70% elongation of the inner region E1 is preferably 1.2 times or greater, more preferably 2 times or greater, and preferably 5 times or less, more preferably 4 times or less, and preferably from 1.2 to 5 times, more preferably from 2 to 4 times, the elongation stress at 70% elongation of the outer region E2.

The elongation stress at 70% elongation of the inner region E1 is preferably 0.25 N or greater, more preferably 0.3 N or greater, and preferably 1.5 N or less, more preferably 1.0 N or less, and preferably from 0.25 to 1.5 N, more preferably from 0.3 to 1.0 N.

The elongation stress at 70% elongation of the outer region E2 is preferably 0.05 N or greater, more preferably 0.15 N or greater, and preferably 1.0 N or less, more preferably 0.5 N or less, and preferably from 0.05 to 1.0 N, more preferably from 0.15 to 0.5 N.

It is preferable that the diaper 1 also has the following configurations.

As regards the elastic members 62 provided to the first leak-proof cuff 6's outwardly-folded portion 65, it is preferable that the number of elastic members 62, in the diaper 1's width direction Y, arranged more toward the free end 6b side than the position P1 of the lateral side edge 43 of the absorbent core 41—i.e., arranged in the lateral extension portion 68—is greater than the number of elastic members arranged more toward the fold-back portion 64 side than the position P1 of the lateral side edge 43 of the absorbent core 41. In the outwardly-folded portion 65, by providing a larger number of elastic members 62 more toward the outer side, in the width direction, than the position P1 of the absorbent core 41's lateral side edge, it is possible to widen the hydrophilic width and secure a wide space G in the crotch portion C, thereby leading to leakage prevention.

In cases where there is an elastic member at the position P1 of the lateral side edge 43 of the absorbent core 41, the elastic member is counted as an elastic member more toward the fold-back portion 64 than the aforementioned position P1 and also counted as an elastic member more toward the free end 6b side than the aforementioned position P1.

It is preferable that all of the elastic members 62 provided to the first leak-proof cuff 6's outwardly-folded portion 65 are provided more toward the free end 6b side than the position of the lateral side edge 43 of the absorbent core 41, including the position of the lateral side edge. Herein, "all of the elastic members 62 are provided more toward the free end 6b side than the position of the lateral side edge 43 of the absorbent core 41, including the position of the lateral side edge" encompasses not only cases where all of the elastic members 62 are arranged only more toward the free end 6b side than the position P1 without having any elastic member overlapping the position P1 of the lateral side edge 43 of the absorbent core 41 (see FIG. 4), but also cases where the elastic member 62a located closest to the fold-back portion 64, among the elastic members 62 provided to the outwardly-folded portion 65, overlaps the position P1 of the lateral side edge 43 of the absorbent core 41 in the diaper 1's width direction Y (see FIG. 6).

In the example illustrated in FIG. 4, none of the elastic members 62 are arranged more toward the fold-back portion 64 than the position P1 of the absorbent core 41's lateral side edge 43, and as a result, there are more elastic members 62 more toward the free end 6b side than the position P1 of the absorbent core 41's lateral side edge 43. Another preferable example is the embodiment illustrated in FIG. 8, wherein there is an elastic member 62 also arranged more toward the fold-back portion 64 than the position P1 of the absorbent core 41's lateral side edge 43, but the number of elastic members 62 arranged more toward the free end 6b side than the position P1 is greater than the number of elastic members 62 arranged more toward the fold-back portion 64 side than the position P1. However, it is preferable to arrange all of the elastic members 62 in the outwardly-folded portion 65 more toward the free end 6b side than the position P1 of the absorbent core 41's lateral side edge 43 as illustrated in FIG. 4, from the viewpoint of preventing elastic members 62 arranged more toward the fold-back portion 64 side than the position P1 from coming into contact with a section more toward the central side (the urination site side), in the width direction, than the wearer's inguinal region K, and thereby preventing reduction in the hydrophilic width.

The difference between the number of elastic members 62 provided more toward the free end 6b side than the position P1 of the lateral side edge 43 of the absorbent core 41 and the number of elastic members provided more toward the fold-back portion 64 side than the aforementioned position P1 is may be one, but is preferably from two to seven, more preferably from three to five. In the embodiment illustrated in FIG. 8, the difference between the number of elastic members is two.

Figure 8:
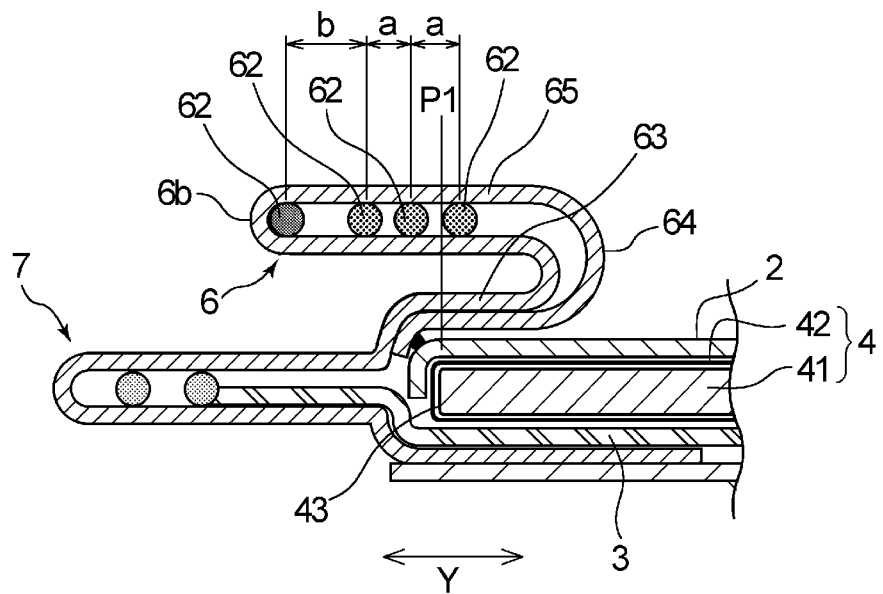
FIG. 8 is a diagram corresponding to FIG. 4, illustrating a principal portion of another embodiment of the present invention.

It is preferable that, among the elastic members 62 provided to the first leak-proof cuff 6's outwardly-folded portion 65, the closer the elastic member is to the free end 6b, the smaller the fineness thereof—i.e., the smaller the diameter of the elastic member. By making the fineness of the elastic members 62 on the fold-back portion 64 side larger than the fineness of the elastic members 62 on the free end 6b side, the elastic members 62 on the fold-back portion 64 side can easily be arranged in the vicinity of the inguinal region K, which makes it possible to widen the hydrophilic width and secure a wide space G in the crotch portion C, thereby leading to leakage prevention. Examples of configurations in which the fineness is reduced more toward the free end 6b side include: configurations in which the diameter of the elastic members 62 decreases in order from the fold-back portion 64 side toward the free end 6b side; and configurations in which some of the adjacent elastic members have the same fineness, but overall, the fineness of elastic members 62 on the free end 6b side tends to be smaller than the fineness of elastic members 62 on the fold-back portion 64 side, as illustrated in FIG. 8 wherein, among the elastic members 62, the three elastic members 62, 62 on the fold-back portion 64 side have a fineness of 620 dtex, whereas the elastic member 62c on the free end 6b side has a fineness of 470 dtex. The difference between the fineness (unit: dtex) of the elastic member 62 closest to the fold-back portion 64 and the fineness (unit: dtex) of the elastic member 62 closest to the free end 6b is preferably from 235 to 620 dtex, more preferably from 310 to 470 dtex. The fineness of the elastic members 62 provided to the first leak-proof cuff 6 is preferably within the range from 235 to 940 dtex, more preferably within the range from 310 to 620 dtex.

It is preferable that, among the elastic members 62 provided to the first leak-proof cuff 6's outwardly-folded portion 65, the closer the elastic member is to the free end 6b, the smaller the elongation rate thereof. By making the elongation rate of the elastic members 62 on the fold-back portion 64 side higher than the elongation rate of the elastic members 62 on the free end 6b side, the elastic members 62 on the fold-back portion 64 side can easily be arranged in the vicinity of the inguinal region K, which makes it possible to widen the hydrophilic width and secure a wide space G in the crotch portion C, thereby leading to leakage prevention. Examples of configurations in which the elongation rate is reduced more toward the free end 6b side include: configurations in which the elongation rate of the elastic members 62 decreases in order from the fold-back portion 64 side toward the free end 6b side; and configurations in which some of the adjacent elastic members have the same elongation rate, but overall, the elongation rate of elastic members 62 on the free end 6b side tends to be lower than the elongation rate of elastic members 62 on the fold-back portion 64 side, as illustrated in FIG. 8 wherein, among the elastic members 62, the three elastic members 62, 62 on the fold-back portion 64 side have an elongation rate of 320%, whereas the elastic member 62c on the free end 6b side has a elongation rate of 280%. The difference between the elongation rate of the elastic member 62 closest to the fold-back portion 64 and the elongation rate of the elastic member 62 closest to the free end 6b is preferably from 20 to 200 percentage points, more preferably from 50 to 100 percentage points. The elongation rate of the elastic members 62 provided to the first leak-proof cuff 6 is preferably from 250 to 400%, more preferably from 280 to 350%.

The elongation rate of the elastic member provided to the outwardly-folded portion 65 is measured as follows.

First, the side seals are torn apart and the absorbent article is spread open, and marks are made in a natural length state at positions indicating a length of 30 mm along the rubber thread. The value Ld for when the elastic member is stretched to its maximum stretched state by holding both ends on the outer sides of the respective marks is employed to calculate the elongation rate according to the following equation.

$$\text{Elongation rate (\%)} = Ld(\text{mm})/30(\text{mm}) \times 100.$$

It is preferable that three or more elastic members 62 are provided to the first leak-proof cuff 6's outwardly-folded portion 65; and the spacing between the elastic members adjacent to one another in the diaper 1's lateral direction Y is the same for all of the elastic members, or becomes longer the closer the elastic members are to the free end 6b. By arranging the elastic members 62 at such intervals in the outwardly-folded portion 65, the outwardly-folded portion 65's inner-side section, wherein the spacing between the elastic members is short, can easily be arranged in the vicinity of the inguinal region K, which makes it possible to widen the hydrophilic width and secure a wide space G in the crotch portion C, thereby leading to leakage prevention.

The embodiments illustrated in FIGS. 4 and 8 are examples wherein the spacing between adjacent elastic members becomes longer the closer the elastic members are to the free end 6b.

Examples of configurations in which the spacing between adjacent elastic members becomes longer the closer the elastic members are to the free end 6b include: configurations in which the spacing between elastic members 62 increases in order from the fold-back portion 64 side toward the free end 6b side; and configurations wherein, overall, the spacing between elastic members on the free end 6b side is longer than the spacing between elastic members on the fold-back portion 64 side, as illustrated in FIG. 8 wherein, among the elastic members 62, the spacing among elastic members is spacing "a" for the three elastic members 62, 62 on the fold-back portion 64 side, whereas the spacing between the two elastic members on the free end 6b side is spacing "b" which is longer than spacing "a". Note that, the spacing between elastic members is the distance, in the width direction, between the respective center positions of the elastic members 62, as in spacing "a" and spacing "b" illustrated in FIG. 8.

Figure 9:
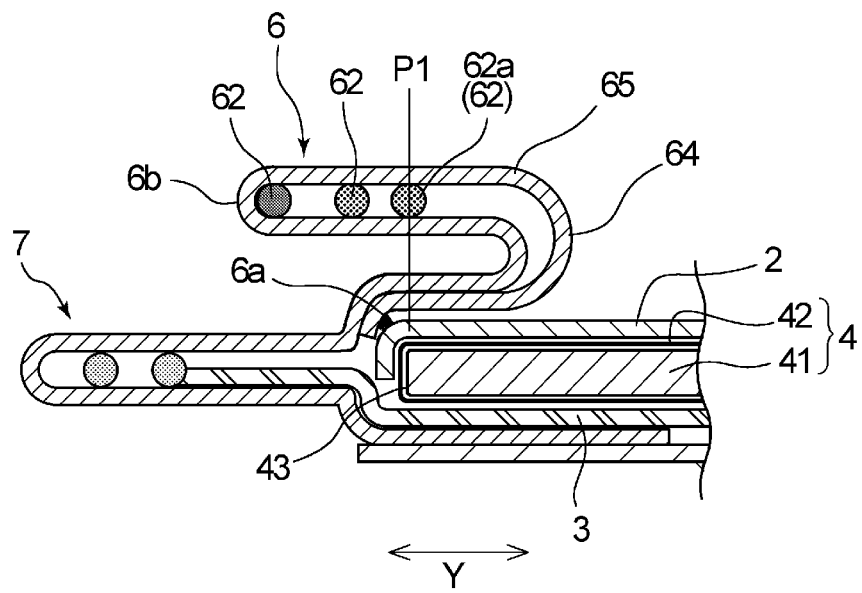
FIG. 9 is a diagram corresponding to FIG. 4, illustrating a principal portion of yet another embodiment of the present invention.

It is also preferable that, as illustrated in FIG. 9, among the elastic members 62 provided to the outwardly-folded portion 65, the elastic member 62a located closest to the fold-back portion 64 overlaps the position P1 of the lateral side edge 43 of the absorbent core 41 in the diaper 1's width direction Y. By arranging the innermost elastic member 62a, which is desirably to be arranged at the inguinal region K, at the position where the rigidity in the diaper 1 changes due to the presence/absence of the absorbent member 4, the first leak-proof cuff 6 can easily be provided with both a stand-up portion and a planar region that contacts the skin in a planar manner. This allows the section where the innermost elastic member 62a is arranged to contact the inguinal region K more easily. Thus, it is possible to widen the hydrophilic width and secure a wide space G in the crotch portion C, thereby leading to leakage prevention.

As illustrated in FIGS. 10(*a*) and 10(*b*), from the viewpoint of preventing the first leak-proof cuff 6's outwardly-folded portion 65 from getting folded toward the central side in the diaper 1's width direction when putting on or while using the diaper 1 and thereby allowing the outwardly-folded portion 65 to easily come into contact in an outwardly-folded state as illustrated in FIG. 6, it is preferable that, among the elastic members 62 provided to the first leak-proof cuff 6, the closer the elastic member is to the free end 6b in the diaper 1's width direction Y, the shorter the length, along the longitudinal direction X, of a range in which the elastic member is fixed in a stretched state to the leak-proof-cuff-forming sheet material 61. Examples of configurations in which the length, along the longitudinal direction X, of the range in which the elastic member is fixed in a stretched state is made shorter the closer the elastic member is to the free end 6b include: configurations in which the length, along the longitudinal direction X, of the range in which the elastic member 62 is fixed in a stretched state is made shorter in order from the fold-back portion 64 side toward the free end 6b side as illustrated in FIG. 10(*b*); and configurations wherein, for some of the elastic members 62, the length, along the longitudinal direction X, of the range in which the respective elastic member 62 is fixed in a stretched state is the same, but overall, the length of the elastic member 62 on the free end 6b side is shorter than the elastic member 62 on the fold-back portion 64 side, as illustrated in FIG. 10(*a*). The absorbent assemblies 5 of FIGS. 10(*a*) and 10(*b*) show only the regions in which the three elastic members 62 provided to the first leak-proof cuff 6 are fixed in a stretched state to the leak-proof-cuff-forming sheet material 61. Within the range in which the elastic member 62 is fixed in a stretched state, the elastic member 62 may be fixed continuously along the longitudinal direction X to the first leak-proof-cuff-forming sheet material 61, or may be fixed intermittently.

The length Lc of the elastic member 62c closest to the free end 6b with respect to the length La of the elastic member 62a closest to the fold-back portion 64 is preferably 70% or greater, more preferably 80% or greater, and preferably 95% or less, more preferably 90% or less, and preferably from 70 to 95%, more preferably from 80 to 90%.

As illustrated in FIGS. 2 and 5, each first leak-proof cuff 6 of the diaper 1 includes, in each of the front portion A and the rear portion B, an end-portion fixed region 66 in which the first leak-proof cuff 6 is fixed so as not to stand up. Further, as illustrated in FIG. 5, the first leak-proof cuff 6's outwardly-folded portion 65 includes a lateral extension portion 68 that extends more toward the outer side, in the width direction Y, than the lateral side edge 43 of the absorbent core 41, and in the end-portion fixed region 66, the outwardly-folded portion 65 is fixed to a lower member 90 located on a lower surface side of the outwardly-folded portion. In each end-portion fixed region 66, the entire region of the lower surface—i.e. the non-skin-facing surface—of the outwardly-folded portion 65 may be joined to the lower member 90 located on the lower surface side thereof, but as illustrated in FIGS. 11(*a*) and 11(*b*), it is preferable that the outwardly-folded portion 65 is fixed to the lower member 90, which is located on the lower surface side of the outwardly-folded portion 65, by a partially joined region 80 in which joined portions 83 are dispersedly arranged.

Preferably, at least the outwardly-folded portion 65's lateral extension portion 68, which extends toward the outer side, in the width direction Y, from the absorbent core 41's lateral side edge 43, is fixed to the lower member 90 by the partially joined region 80 in which the joined portions 83 are dispersedly arranged. Further, preferably, as illustrated in FIG. 11(*b*), the partially joined region 80 includes the joined portions 83 and non-joined portions 84 alternately in one direction in a planar view of the outwardly-folded portion 65 and in a direction orthogonal to the one direction. The "one direction and the orthogonal direction thereto" may refer, for example, to the diaper 1's longitudinal direction X and width direction Y as illustrated in FIG. 11(*b*), but are not limited thereto. The joined portions 83 in the partially joined region 80 are portions where the outwardly-folded portion 65 and the lower member 90 are joined together by a known joining method such as an adhesive, heat-sealing, ultrasonic sealing, or high-frequency sealing. The non-joined portions 84 are sections where the outwardly-folded portion 65 and the lower member 90 are not joined together.

By fixing at least the lateral extension portion 68 of the outwardly-folded portion 65 to the lower member 90 in one or both of the front portion A and the rear portion B, the outwardly-folded portion 65 can be prevented from inward-folding, i.e., from getting folded inwardly toward the central side in the diaper 1's width direction. Further, by joining the lateral extension portion 68 of the outwardly-folded portion 65 to the lower member 90 by the partially joined region 80 in one or both of the front portion A and the rear portion B, it is also possible to prevent deterioration of the first leak-proof cuff 6's texture to the touch while preventing the aforementioned inward-folding.

As illustrated in FIG. 5, the diaper 1's outwardly-folded portion 65 includes the aforementioned lateral extension portion 68 that extends more toward the outer side, in the width direction Y, than the lateral side edge 43 of the absorbent core 41. From the viewpoint of providing a soft texture to the surface that comes into contact with the skin, it is preferable that, in one or both of the front portion A and the rear portion B, the lateral extension portion 68 is joined to a lower member 90 located on the lower surface side of the outwardly-folded portion 65 in an area occupying preferably from 2 to 30%, more preferably from 5 to 25%, of the area of an opposition region in which the outwardly-folded portion 65 opposes the lower member 90.

Further, as illustrated in FIG. 5, the diaper 1's outwardly-folded portion 65 is joined to the lower member 90 both at the lateral extension portion 68, which extends more toward the outer side, in the width direction Y, than the lateral side edge 43 of the absorbent core 41, and also at a section of the outwardly-folded portion 65 that opposes the inwardly-oriented portion 63. However, from the viewpoint of providing a soft texture to the surface that comes into contact with the skin, it is also preferable that the outwardly-folded portion 65 is not joined to the inwardly-oriented portion 63 opposing the outwardly-folded portion 65.

Figure 11A:
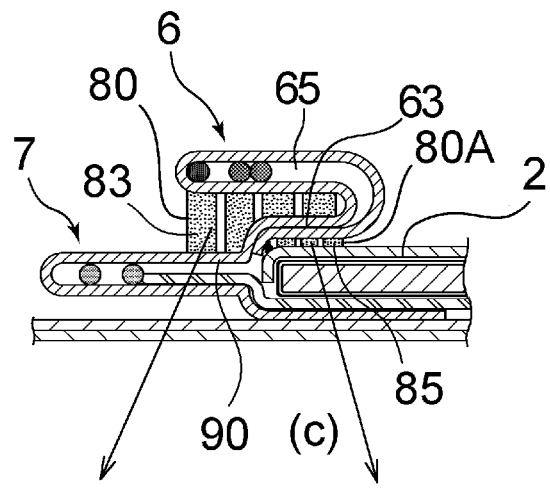
Figure 11B:
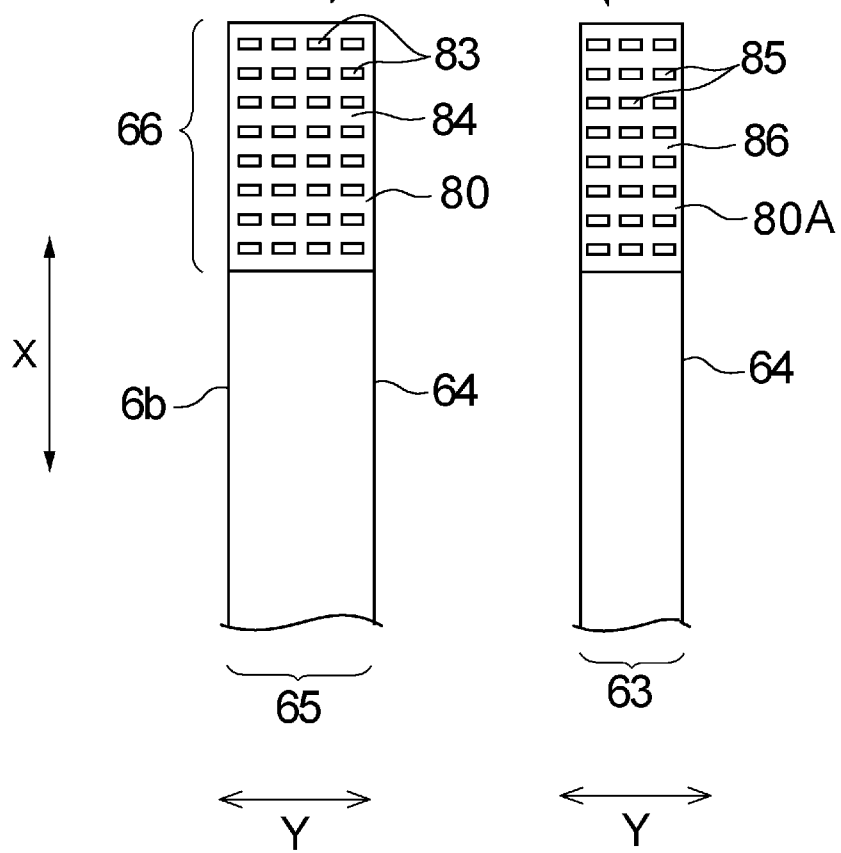
Figure 12A:
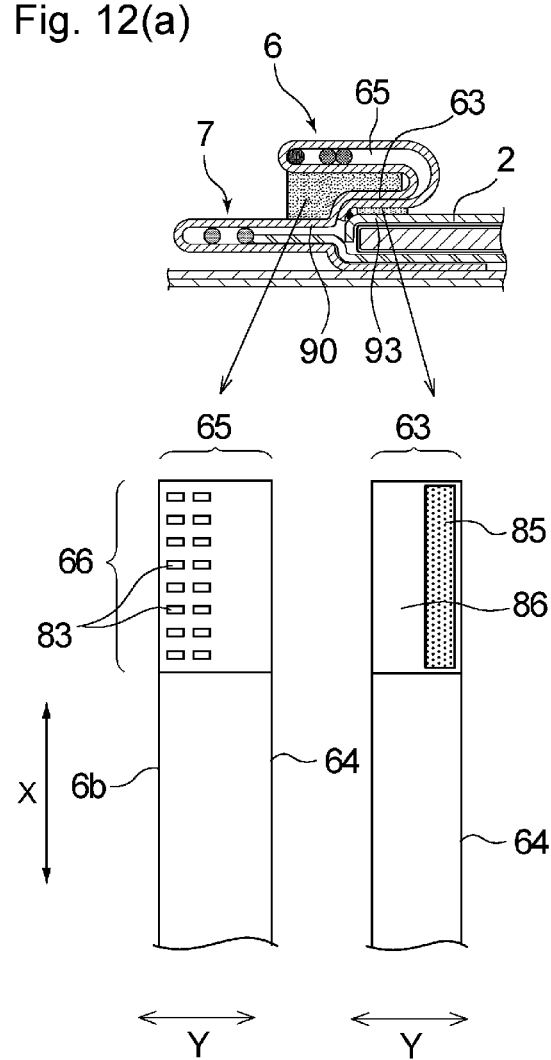
FIG. 12(a) is a diagram illustrating another example of an arrangement of joined portions that join the outwardly-folded portion and inwardly-oriented portion to respective lower members which are located on the lower surface side of the respective portions.
Figure 12B:
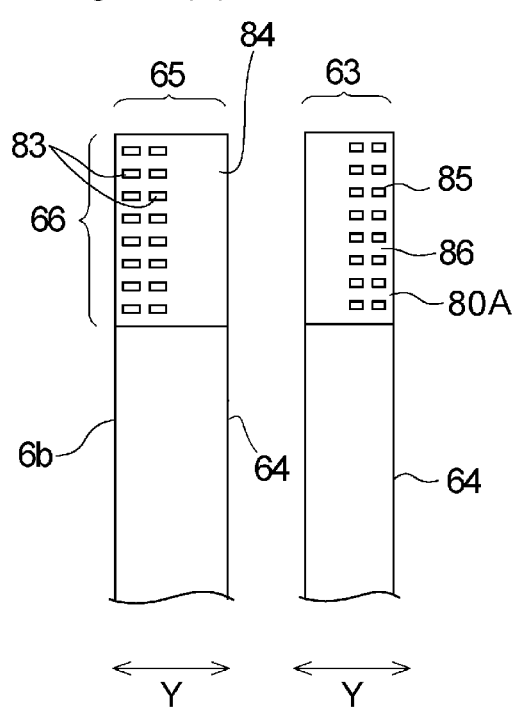
FIG. 12(b) is a diagram illustrating yet another example of an arrangement of joined portions that join the outwardly-folded portion and inwardly-oriented portion to respective lower members which are located on the lower surface side of the respective portions.

As illustrated in FIG. 11(*c*), it is preferable that, in each end-portion fixed region 66 of the front portion A and the rear portion B, the lower surface—i.e. the non-skin-facing surface—of the first leak-proof cuff 6's inwardly-oriented portion 63 is joined to the topsheet 2 located on the lower surface side of the inwardly-oriented portion. The inwardly-oriented portion 63 and the topsheet 2 may be joined together by: joining by a partially joined region 80A in which joined portions 85 are dispersedly arranged as illustrated in FIGS. 11(a), 11(c), and 12(b); or by joining by a single joined portion 85 having a certain amount of area as illustrated in FIG. 12(a). It is preferable that the partially joined region 80A, which joins the inwardly-oriented portion 63 and the topsheet 2 together, also includes the joined portions 85 and non-joined portions 86 alternately in one direction in a planar view and in a direction orthogonal to the one direction. The "one direction and the orthogonal direction thereto" may refer, for example, to the diaper 1's longitudinal direction X and width direction Y as illustrated in FIG. 11(c), but are not limited thereto. The joined portions 85 in the partially joined region 80A are portions where the inwardly-oriented portion 63 and the topsheet 2 etc. are joined together by a known joining method such as an adhesive, heat-sealing, ultrasonic sealing, or high-frequency sealing. The non-joined portions 86 are sections where the inwardly-oriented portion 63 and the topsheet 2 etc. are not joined together.

In cases where the first leak-proof cuff 6's outwardly-folded portion 65 is joined by the joined portions 83 to the lower member 90, which is located on the lower surface side of the outwardly-folded portion, in the end-portion fixed region 66 of one or both of the front portion A and the rear portion B as illustrated in FIG. 5 or FIG. 11(a), it is preferable that, as in the outwardly-folded portion 65 illustrated in FIGS. 12(a) and 12(b), the area of the joined portions 83 is larger on the outwardly-folded portion 65's outer side in the width direction Y than on the inner side. The "outwardly-folded portion 65's outer side in the width direction Y" is the free end 6b side of the outwardly-folded portion 65, and the "outwardly-folded portion 65's inner side in the width direction Y" is the fold-back portion 64 side of the outwardly-folded portion 65.

By joining the outwardly-folded portion 65 to the lower member 90 according to the aforementioned configuration in one or both of the front portion A and the rear portion B, the outwardly-folded portion 65 can be prevented more effectively from inward-folding, i.e., from getting folded inwardly toward the central side in the diaper 1's width direction. The joined portion 83 joining the outwardly-folded portion 65 to the lower member 90 located on the lower surface side thereof corresponds to the "first joined portion" according to the invention.

The "area of the first joined portions 83" is the total area of the first joined portions 83 which are joined portions joining the first leak-proof cuff 6's outwardly-folded portion 65 and the lower member 90 in each end-portion fixed region 66 present in the front portion A or the rear portion B.

On the other hand, in cases where the first leak-proof cuff 6's inwardly-oriented portion 63 is joined by the joined portion(s) 85 to the topsheet 2 located on a lower surface side of the inwardly-oriented portion in the end-portion fixed region 66 of one or both of the front portion A and the rear portion B as illustrated in FIG. 5 or FIG. 11(a), it is preferable that, as in the inwardly-oriented portion 63 illustrated in FIGS. 12(a) and 12(b), the area of the joined portion(s) 85 is larger on the inner side in the width direction Y than on the outer side. The "outer side in the width direction Y" is the lateral side edge 43 side of the absorbent core 41 in the width direction Y, and the "inner side in the width direction Y" is the fold-back portion 64 side in the width direction Y.

By joining the inwardly-oriented portion 63 to the topsheet 2 according to the aforementioned configuration in one or both of the front portion A and the rear portion B, the fold-back portion 64 side of the first leak-proof cuff 6 can be effectively prevented from peeling off from the topsheet 2, and also, the first leak-proof cuff 6's softness and texture to the touch can be improved. The joined portion 85 joining the inwardly-oriented portion 63 to the lower member 93, such as the topsheet 2, located on the lower surface side thereof corresponds to the "second joined portion" according to the invention.

As illustrated in FIGS. 12(a) and 12(b), it is preferable that, in the end-portion fixed region 66 of one or both of the front portion A and the rear portion B, the first leak-proof cuff 6's outwardly-folded portion 65 is joined by the first joined portions 83 to the lower member 90 located on the lower surface side of the outwardly-folded portion 65, and the inwardly-oriented portion 63 is joined by the second joined portion(s) 85 to the topsheet 2 opposing the inwardly-oriented portion 63. In this case, it is preferable that the area of the first joined portions 83 is smaller than the area of the second joined portion(s) 85, because in this way, the first leak-proof cuff 6 can be firmly fixed at a section distant from the wearer's skin, while being able to further improve softness and texture to the touch in sections of the first leak-proof cuff 6 that come into contact with the skin. The "area of the second joined portion(s) 85" is the total area of the second joined portion(s) 85 serving as joined portion(s) joining the first leak-proof cuff 6's inwardly-oriented portion 63 and the lower member 93, such as the topsheet 2 located on the lower surface side, in each end-portion fixed region 66 present in the front portion A or the rear portion B.

Figure 13:
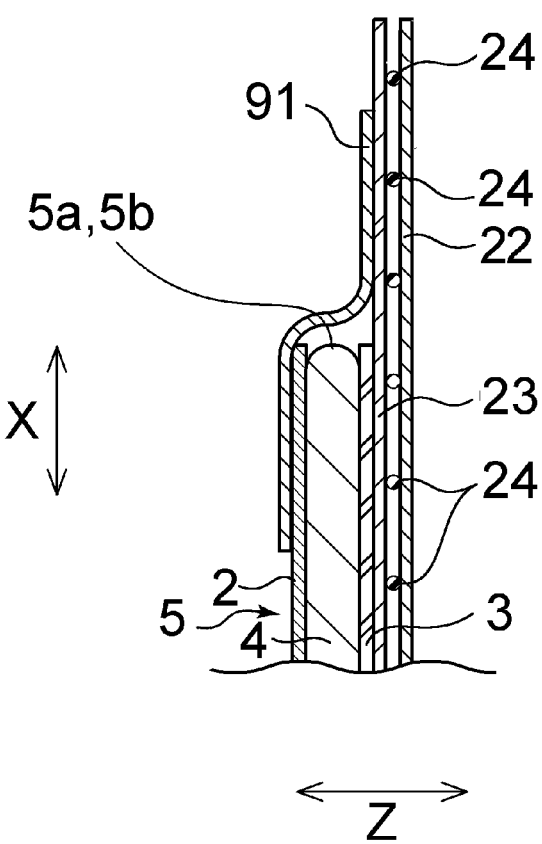
FIG. 13 is a cross-sectional view illustrating a principal portion of another embodiment of the present invention, and is a cross-sectional view, along the longitudinal direction, ranging from the waist opening to a portion of the absorbent assembly in a central section, in the width direction, of the rear portion or the front portion.
Figure 14A:
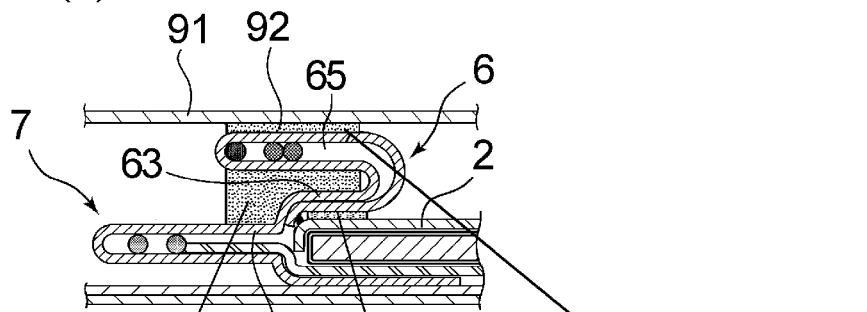
FIG. 14(a) is a cross-sectional view illustrating a fundamental configuration of a principal portion of yet another embodiment of the present invention.
Figure 14B:
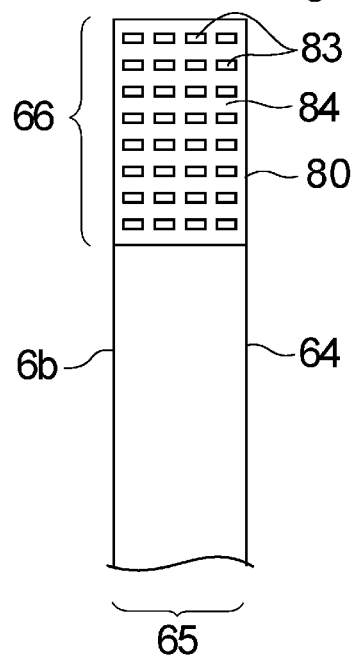
FIG. 14(b) is a plan view of an outwardly-folded portion illustrating an example of an arrangement of joined portions that join the outwardly-folded portion to a lower member located on the lower surface side thereof.
Figure 14C:
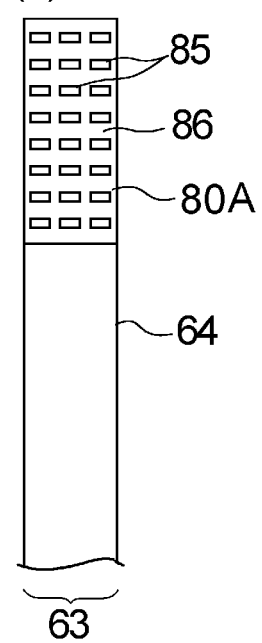
FIG. 14(c) is a plan view of an inwardly-oriented portion illustrating an example of an arrangement of joined portions that join the inwardly-oriented portion to a lower member located on the lower surface side thereof.
Figure 14D:
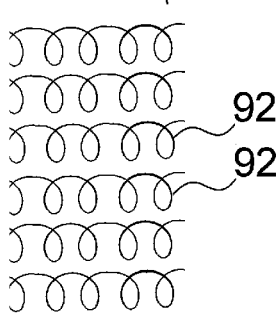
FIG. 14(d) is a plan view illustrating an example of an arrangement of joined portions that join a cover nonwoven fabric to the outwardly-folded portion located on the lower surface side thereof.

In the disposable diaper of the present invention, as illustrated in FIG. 13, it is also preferable that a cover nonwoven fabric 91 that covers the skin-facing surface side of the absorbent assembly 5 is provided to an end portion 5a, 5b, in the longitudinal direction, of the absorbent assembly 5 in one or both of the front portion A and the rear portion B. Providing the cover nonwoven fabric 91 can prevent such problems as the absorbent assembly 5's end portion, in the longitudinal direction, getting lifted up as a result of a portion of the wearer's body coming into contact with the absorbent assembly's end portion when putting on the diaper. In either of the front portion A and the rear portion B, it is preferable to arrange the cover nonwoven fabric 91 so as to extend between the pair of side seals S, S. Also, as illustrated in FIG. 13, it is preferable to arrange the cover nonwoven fabric so as to cover the absorbent assembly 5's respective end portion 5a, 5b in the longitudinal direction in a manner extending from the inner side to the outer side in the longitudinal direction X. The cover nonwoven fabric 91 may be a sheet that is separate from both the outer sheet 22 and the inner sheet 23 as illustrated in FIG. 13, or, although not illustrated, may be formed by a sheet that is continuous with the outer sheet 22 folded back toward the skin-facing surface side at the peripheral edge of the waist opening 8.

In cases of providing the cover nonwoven fabric 91, it is preferable that, from the viewpoint of maintaining the cover nonwoven fabric 91's soft texture, the skin-facing surface side of the first leak-proof cuff 6's outwardly-folded portion 65 is joined by third joined portions 92 to the cover nonwoven fabric 91; and the area (total area) of the first joined portions 83 joining the first leak-proof cuff 6's outwardly-folded portion 65 to the lower member 90, as well as that of the second joined portion(s) 85 joining the first leak-proof cuff 6's inwardly-oriented portion 63 to the topsheet 2, is larger than the area of the third joined portions 92, as illustrated in FIG. 14. The third joined portions 92 do not include joined portions that join the cover nonwoven fabric 91 to sections other than the outwardly-folded portion 65. For example, the third joined portions 92 may preferably be joined portions formed by an adhesive applied in any discretionary pattern, such as a spiral, striped, dotted (scattered) or wavy (undulating) pattern, or may preferably be fusion-bonded portions formed in a scattered manner by scattered dots by heat-sealing, high-frequency sealing, ultrasonic sealing, etc. For the cover nonwoven fabric, any discretionary nonwoven fabric made by one of various manufacturing methods may be used; it is, however, preferable to use a nonwoven fabric having a good texture to the touch, and preferable to use, for example, an air-through nonwoven fabric or a spunbond nonwoven fabric.

As illustrated in FIGS. 2 to 4, the diaper 1 illustrated in FIG. 1 includes the second leak-proof cuffs 7 each including a second leak-proof-cuff-forming sheet material 71 and second elastic members 72, 72 fixed in a stretched state to the sheet material 71 along the longitudinal direction X, the second leak-proof cuffs 7 being respectively provided widthwisely outside of the first leak-proof cuffs 6 that are provided respectively to the absorbent assembly 5's both lateral sides along the longitudinal direction. It is preferable that the length L5 of each second leak-proof cuff 7 from the lateral side edge 43 of the absorbent core 41 to the second elastic member 72a is longer than the total length of the length L2 of the inwardly-oriented portion 63 of the first leak-proof cuff 6 and the length L6 from the fold-back portion 64 to the elastic member 62a provided to the outwardly-folded portion 65. By making the length L5 of the second leak-proof cuff 7 longer than the total length of the lengths L2 and L6—which corresponds to the length from the first leak-proof cuff 6's base end 6a up to the elastic member 62a provided most inwardly, in the width direction, of the outwardly-folded portion 65—the second leak-proof cuff 7 supports the rising of the first leak-proof cuff 6 from outside and thereby covers the first leak-proof cuff 6. This improves leakage prevention performance and eliminates concerns over leakage. Further, it is possible to prevent the width of the space G (see FIG. 6) formed in the crotch portion C from becoming narrow as a result of the second leak-proof cuff 7's elastic members pressing, from outside, a region between the first leak-proof cuff 6's base end 6a and the outwardly-folded portion 65's elastic member 62a provided most inwardly in the width direction.

From the aforementioned viewpoints, the length L5 with respect to the total length of the lengths L2 and L6 is preferably 105% or greater, more preferably 110% or greater, and preferably 180% or less, more preferably 150% or less, and preferably from 105 to 180%, more preferably from 110 to 150%.

The lengths L1 to L6 are each measured along the disposable diaper's width direction Y in a state where the disposable diaper is spread-open and stretched.

It should be noted that, in cases where the first leak-proof cuff 6's outwardly-folded portion 65 includes a plurality of elastic members 62, the aforementioned total length of the lengths L2 and L6 is defined as the length from the first leak-proof cuff 6's base end 6a up to the elastic member 62a provided most inwardly, in the width direction, of the outwardly-folded portion 65. Further, in cases where the second leak-proof cuff 7 includes a plurality of second elastic members 72, the aforementioned length L5 is defined as the length from the absorbent core 41's lateral side edge 43 up to the second elastic member 72a provided most inwardly, in the width direction, of the second leak-proof cuff 7.

The length L5 is preferably 15 mm or greater, more preferably 20 mm or greater, and preferably 50 mm or less, more preferably 40 mm or less, and preferably from 15 to 50 mm, more preferably from 20 to 40 mm.

The total length of the lengths L2 and L6 is preferably 10 mm or greater, more preferably 15 mm or greater, and preferably 45 mm or less, more preferably 30 mm or less, and preferably from 10 to 45 mm, more preferably from 15 to 30 mm.

From the viewpoint of not excessively pressing the first leak-proof cuff 6 from outside, the number of second elastic members 72 provided to the second leak-proof cuff 7 is preferably from one to five, more preferably from two to four.

The elastic region E3 (see FIG. 4) of the second leak-proof cuff 7 preferably has a higher elongation stress at 70% elongation than the outer region E2 of the first leak-proof cuff 6. The elastic region E3 of the second leak-proof cuff 7 is a region between: an inner end portion, in the width direction, of the elastic member 72a arranged most inward, in the width direction, among the plurality of elastic members fixed in a stretched state along the longitudinal direction X to the second leak-proof-cuff-forming sheet material; and an outer end portion, in the width direction, of the elastic member 72c arranged most outward, in the width direction.

By making the elongation stress of the second leak-proof cuff 7's elastic region E3 higher than the first leak-proof cuff 6's outer region E2, the second leak-proof cuff 7 can support the rising of the first leak-proof cuff 6, thereby improving coverability of the first leak-proof cuff 6 and thus improving leakage prevention performance while eliminating concerns over leakage.

{Method for Measuring Elongation Stress at 70% Elongation of Elastic Region E3 of Second Leak-Proof Cuff}

Figure 7B:
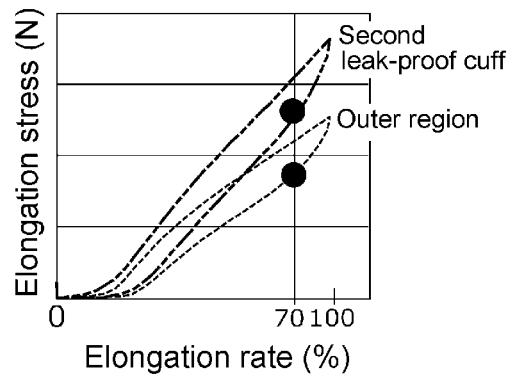

A stress-strain curve (S-S curve) is created (see FIG. 7(b)), as in the aforementioned method for measuring the elongation stress at 70% elongation of the inner region E1 and outer region E2. The stress at the point where the elongation rate in the contraction process is 70% is read from the curve, and this is considered the stress at 70% elongation of the elastic region E3. Note that the measurement sample employed in this method is a sample of the elastic region E3 cut out from the second leak-proof cuff 7, the measurement sample having a length in the longitudinal direction X equivalent to the entire length of the second leak-proof cuff 7 in the longitudinal direction X and having a length in the width direction Y equivalent to the width of the elastic region E3.

The elongation stress at 70% elongation of the elastic region E3 of the second leak-proof cuff is preferably 1.2 times or greater, more preferably 2 times or greater, and preferably 5 times or less, more preferably 4 times or less, and preferably from 1.2 to 5 times, more preferably from 2 to 4 times, the elongation stress at 70% elongation of the outer region E2 of the first leak-proof cuff 6.

The elongation stress of the elastic region E3 of the second leak-proof cuff 7 is preferably 0.2 N or greater, more preferably 0.3 N or greater, and preferably 1.5 N or less, more preferably 1.0 N or less, and preferably from 0.2 to 1.5 N, more preferably from 0.3 to 1.0 N.

It is preferable that the elongation stress at 70% elongation of the elastic region E3 of the second leak-proof cuff and the elongation stress at 70% elongation of the inner region E1 of the first leak-proof cuff are substantially the same, or the elongation stress at 70% elongation of the inner region E1 of the first leak-proof cuff 6 is greater.

Figure 15:
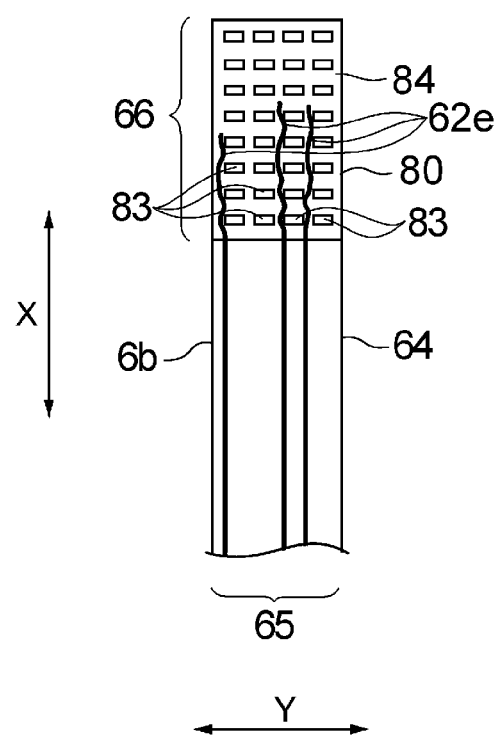
FIG. 15 is a diagram illustrating a principal portion of yet another embodiment of the present invention, and is a projective view illustrating a projection, along the diaper's thickness direction, of a range from the outwardly-folded portion's skin-facing surface side to a lower member located on the lower surface side of the outwardly-folded portion.

As described above, it is preferable that, in the end-portion fixed region 66 in one or both of the front portion A and the rear portion B, the outwardly-folded portion 65 is fixed to the lower member 90, which is located on the lower surface side of the outwardly-folded portion 65, by a partially joined region 80 in which the joined portions 83 are dispersedly arranged. It is also preferable that the elastic member 62 provided to the outwardly-folded portion 65 has, at an end portion in the longitudinal direction, a free end portion whose stretched state has been released. In this case, as illustrated in FIG. 15, it is preferable that, in a planar view of the outwardly-folded portion 65 of the diaper in a spread-open and stretched state, the free end portion 62*e* of the elastic member 62 having such a free end portion is arranged in a manner overlapping a non-joined portion 84 within the partially joined region 80. Furthermore, it is preferable that the free end portion 62*e* of the elastic member 62 is arranged so as to pass between joined portions 83, within the partially joined region 80, that are separated from one another in a direction intersecting with the diaper's longitudinal direction X. Typically, the "direction intersecting with the longitudinal direction X" is the width direction Y orthogonal to diaper's longitudinal direction X but is not limited thereto, and may be, for example, a direction intersecting with the longitudinal direction X at an angle of from 30 to 90 degrees, preferably from 45 to 90 degrees.

In the diaper 1 illustrated in FIG. 1, as illustrated in FIGS. 3 and 4, the leak-proof-cuff-forming sheet material 61 in the first leak-proof cuff 6 is a sheet material having a two-layer structure, and the leak-proof-cuff-forming sheet material 71 in the second leak-proof cuff 7 is a sheet material including: a two-layer section constituted by two layers of nonwoven fabric; and a three-layer section including a two-layer section constituted by two layers of nonwoven fabric, and the backsheet interposed between the two layers of nonwoven fabric. The leak-proof-cuff-forming sheet material 61 in the first leak-proof cuff 6, however, may instead be a sheet material including: a two-layer section constituted by two layers of nonwoven fabric; and a three-layer section wherein a sheet having water-imperviousness similar to the backsheet is interposed between the two layers of nonwoven fabric. Alternatively, one or both of the first leak-proof cuff 6 and the second leak-proof cuff 7 may include, between the two layers of nonwoven fabric, a water-impervious layer formed by a water-insoluble adhesive bonded to one or the other of the nonwoven fabric layers. By providing the first leak-proof cuff 6 with a water-impervious sheet or a water-impervious layer made of a water-insoluble adhesive etc. between the two layers of nonwoven fabric, it is possible to reliably prevent liquid components, such as urine and feces, from passing through the first leak-proof cuff 6 and leaking out.

Materials for forming the diaper 1 are described below.

For the materials for forming the various parts of the diaper 1, various types of materials used as the respective parts in conventional disposable diapers can be used without particular limitation. For example, for the topsheet 2, it is possible to use a hydrophilic, liquid-permeable single-layer or multilayer nonwoven fabric or a perforated resin film. For the backsheet 3, it is possible to use a moisture-permeable or moisture-impermeable resin film or a laminate of the resin film and a nonwoven fabric.

For the fibers constituting the fiber aggregate constituting the absorbent core 41, it is possible use, for example, hydrophilic fibers such as pulp fiber, rayon fiber, cotton fiber or cellulose acetate, polyolefin-based fibers such as polyethylene or polypropylene, or condensation fibers such as polyesters or polyamides. It is preferable that the fiber aggregate is obtained by a fiber stacking step wherein a fiber material supplied on an airflow is sucked and stacked in a depression having a predetermined shape. A functional material may be mixed and stacked together with the fiber material. For example, the functional material may be retained by being sandwiched between two fiber aggregates, or retained among the fibers by mixing and stacking therewith. A single type, or a combination of two or more types, of the fiber, as well as the functional material such as the water-absorbent polymer, may be used. Examples of the water-absorbent polymer include particles of sodium polyacrylate, acrylic acid/vinyl alcohol copolymer, crosslinked sodium polyacrylate, starch/acrylic acid graft copolymer, isobutylene/maleic anhydride copolymer and saponified products thereof, or polyaspartic acid. For the core-wrap sheet, any type of known sheets may be used, with preferable examples including thin paper, such as tissue paper, and water-permeable nonwoven fabric.

For the nonwoven fabrics constituting the respective first and second leak-proof-cuff-forming sheet materials 61, 71, it is possible to use any type of known nonwoven fabric conventionally used for leak-proof cuffs, with examples including spunbond nonwoven fabric, spunbond-meltblown-spunbond (SMS) laminate nonwoven fabric, spunbond-meltblown-meltblown-spunbond (SMMS) nonwoven fabric, heat-rolled nonwoven fabric, and air-through nonwoven fabric.

The nonwoven fabric constituting the first cuff-forming sheet material 61 has a bulk softness of preferably from 3 to 7 cN, more preferably from 4 to 6 cN. Further, the nonwoven fabric is preferably a SMS nonwoven fabric having a three-layer structure in which a spunbond nonwoven fabric layer, a meltblown nonwoven fabric, and a spunbond nonwoven fabric are layered in order.

In cases where a nonwoven fabric with a low bulk softness is used, the first leak-proof cuff 6 becomes soft, and thus folds and creases are likely to be created in unexpected places. With the disposable diaper of the present invention, however, the effects of the present invention can be attained even when a soft nonwoven fabric is used, and thus, the feel of the first leak-proof cuff 6 against the skin can be further improved.

Similarly for the nonwoven fabric constituting the second cuff-forming sheet material 71, it is preferable to use a nonwoven fabric having a bulk softness of from 3 to 7 cN.

The elastic members provided to the first leak-proof cuff 6 and the second leak-proof cuff 7 may be shaped preferably in a thread shape (rubber threads etc.) or rubber bands with a predetermined width (such as rubber tapes), and preferably in a thread shape. Examples of materials for the elastic members provided in the various parts include natural rubber, synthetic rubber such as styrene-butadiene, butadiene, isoprene and neoprene, EVA, extensible polyolefins, and urethane.

Preferred embodiments of the present invention have been described above, but the present invention is not limited to the foregoing embodiments, and various modifications can be made within a scope that does not depart from the gist of the invention.

For example, the disposable diaper of the disclosure is a pull-on disposable diaper wherein the outer cover 10 is divided into a rear panel to be arranged on the wearer's rear side and a front panel to be arranged on the front side, and the absorbent assembly is fixed in a manner bridging the rear panel and the front panel. The disposable diaper, however, may be a so-called open-type disposable diaper wherein fastening tapes are provided in the rear portion, and the diaper is worn by fastening the fastening tapes to a landing tape provided on the outer surface in the front portion. In an open-type disposable diaper, the crotch portion is the section in which concave cutout portions conforming to the shape of the periphery of the respective legs are formed in the respective lateral side edges, and the rear portion and the front portion are sections located respectively in the rear and front of the crotch portion.

The second leak-proof cuff 7 of the diaper 1 in the foregoing embodiments may include only one elastic member. Alternatively, the second leak-proof cuff 7 itself may be omitted. Further, the section of the absorbent core 41 located in the crotch portion may be divided into a plurality of parts, such as two or three parts, as illustrated in FIG. 6.

In relation to the foregoing embodiments, the description further discloses the following disposable diapers.

{1}

A disposable diaper having a longitudinal direction along a front-rear direction of a wearer and a width direction orthogonal to the longitudinal direction, the disposable diaper including a rear portion to be arranged on the wearer's rear side when worn, a front portion to be arranged on the wearer's front side and a crotch portion located between the rear portion and the front portion, the disposable diaper comprising:

an absorbent assembly including a topsheet, a backsheet and an absorbent member that is interposed between the topsheet and the backsheet and that includes an absorbent core; and a pair of leak-proof cuffs provided respectively to the absorbent assembly's both lateral sides along the longitudinal direction, wherein:

each of the leak-proof cuffs includes a leak-proof-cuff-forming sheet material and elastic members fixed to the sheet material, and includes an inwardly-oriented portion wherein the sheet material is arranged from a lateral side edge of the absorbent core toward the absorbent member's inner side in the width direction, a fold-back portion where the sheet material is folded back toward the absorbent member's outer side in the width direction, the fold-back portion being located above the absorbent member, and an outwardly-folded portion ranging from the fold-back portion to a free end of the leak-proof cuff;

the outwardly-folded portion has a length, in the width direction, that is longer than the length of the inwardly-oriented portion;

the plurality of elastic members are fixed in a stretched state to the outwardly-folded portion along the longitudinal direction;

the free end of the leak-proof cuff is located widthwisely outside of the lateral side edge of the absorbent core; and in the outwardly-folded portion, in a case where a region where the plurality of elastic members are provided is divided, in the outwardly-folded portion's width direction, into two equal parts defined respectively as an inner region and an outer region, the inner region has a higher elongation stress at 70% elongation than the outer region.

{2}

The disposable diaper as set forth in clause {1}, wherein, as regards the elastic members provided to the outwardly-folded portion, the number of elastic members, in the width direction, arranged more toward the free end side than the position of the lateral side edge of the absorbent core is greater than the number of elastic members arranged more toward the fold-back portion side than the position of the lateral side edge of the absorbent core.

{3}

The disposable diaper as set forth in clause {1} or {2}, wherein the number of elastic members to be provided to the outwardly-folded portion is preferably two or greater, more preferably three or greater, and preferably ten or fewer, more preferably five or fewer.

{4}

The disposable diaper as set forth in any one of clauses {1} to {3}, wherein the difference between the number of elastic members provided more toward the free end side than the position of the lateral side edge of the absorbent core and the number of elastic members provided more toward the fold-back portion side than the aforementioned position is preferably from two to seven, more preferably from three to five.

{5}

The disposable diaper as set forth in any one of clauses {1} to {4}, wherein, among the elastic members provided to the outwardly-folded portion, the closer the elastic member is to the free end, the smaller the fineness thereof.

{6}

The disposable diaper as set forth in any one of clauses {1} to {5}, wherein, among the plurality of elastic members, the difference between the fineness of the elastic member closest to the fold-back portion and the fineness of the elastic member closest to the free end is preferably from 235 to 620 dtex, more preferably from 310 to 470 dtex.

{7}

The disposable diaper as set forth in any one of clauses {1} to {6}, wherein the fineness of the elastic member provided to the leak-proof cuff is preferably from 235 to 940 dtex, more preferably from 310 to 620 dtex.

{8}

The disposable diaper as set forth in any one of clauses {1} to {7}, wherein, among the elastic members provided to the outwardly-folded portion, the closer the elastic member is to the free end, the smaller the elongation rate thereof.

{9}

The disposable diaper as set forth in any one of clauses {1} to {8}, wherein, among the plurality of elastic members, the difference between the elongation rate of the elastic member closest to the fold-back portion and the elongation rate of the elastic member closest to the free end is preferably from 20 to 200 percentage points, more preferably from 50 to 100 percentage points.

{10}

The disposable diaper as set forth in any one of clauses {1} to {9}, wherein the elongation rate of the elastic member provided to the leak-proof cuff is preferably from 250 to 400%, more preferably from 280 to 350%.

{11}

The disposable diaper as set forth in any one of clauses {1} to {10}, wherein:

three or more elastic members are provided to the outwardly-folded portion; and a spacing between the elastic members adjacent to one another in the width direction is the same for all of the elastic members, or becomes longer the closer the elastic members are to the free end.

{12}

The disposable diaper as set forth in any one of clauses {1} to {11}, wherein all of the elastic members provided to the outwardly-folded portion are provided more toward the free end side than the position of the lateral side edge of the absorbent core, including the position of the lateral side edge.

{13}
The disposable diaper as set forth in any one of clauses {1} to {12}, wherein, among the elastic members provided to the outwardly-folded portion, the elastic member located closest to the fold-back portion overlaps the position of the lateral side edge of the absorbent core in the width direction.

{14}
The disposable diaper as set forth in any one of clauses {1} to {13}, wherein, among the elastic members, the closer the elastic member is to the free end, the shorter the length, along the longitudinal direction, of a range in which the elastic member is fixed in a stretched state.

{15}
The disposable diaper as set forth in any one of clauses {1} to {14}, wherein:
the leak-proof cuff includes, in each of the front portion and the rear portion, an end-portion fixed region in which the leak-proof cuff is fixed so as not to stand up;
the outwardly-folded portion includes a lateral extension portion that extends more toward the outer side, in the width direction, than the lateral side edge of the absorbent core; and
in the end-portion fixed region of one or both of the front portion and the rear portion, the lateral extension portion is fixed by a partially joined region, in which joined portions are dispersedly arranged, to a lower member located on a lower surface side of the lateral extension portion.

{16}
The disposable diaper as set forth in any one of clauses {1} to {15}, wherein:
the leak-proof cuff includes, in each of the front portion and the rear portion, an end-portion fixed region in which the leak-proof cuff is fixed so as not to stand up;
in the end-portion fixed region of one or both of the front portion and the rear portion, the outwardly-folded portion is joined by a first joined portion to a lower member located on a lower surface side of the outwardly-folded portion; and
in the outwardly-folded portion, an area of the first joined portion is larger on the outer side in the width direction than on the inner side.

{17}
The disposable diaper as set forth in any one of clauses {1} to {16}, wherein:
the leak-proof cuff includes, in each of the front portion and the rear portion, an end-portion fixed region in which the leak-proof cuff is fixed so as not to stand up;
in the end-portion fixed region of one or both of the front portion and the rear portion, the inwardly-oriented portion is joined by a second joined portion to a lower member located on a lower surface side of the inwardly-oriented portion; and
in the inwardly-oriented portion, an area of the second joined portion is larger on the inner side in the width direction than on the outer side.

{18}
The disposable diaper as set forth in any one of clauses {1} to {17}, wherein:
the leak-proof cuff includes, in each of the front portion and the rear portion, an end-portion fixed region in which the leak-proof cuff is fixed so as not to stand up;
in the end-portion fixed region of one or both of the front portion and the rear portion, the outwardly-folded portion is joined by a first joined portion to a lower member located on the lower surface side of the outwardly-folded portion, and the inwardly-oriented portion is joined by a second joined portion to the topsheet located on the lower surface side of the inwardly-oriented portion; and
an area of the first joined portion is smaller than an area of the second joined portion.

{19}
The disposable diaper as set forth in clause {18}, wherein:
a cover nonwoven fabric that covers a skin-facing surface side of the absorbent assembly is provided to an end portion, in the longitudinal direction, of the absorbent assembly in one or both of the front portion and the rear portion;
the outwardly-folded portion of the leak-proof cuff is joined by a third joined portion to the cover nonwoven fabric; and
the area of each of the first joined portion and the second joined portion is larger than an area of the third joined portion.

{20}
The disposable diaper as set forth in any one of clauses {1} to {19}, wherein:
the leak-proof cuff includes, in each of the front portion and the rear portion, an end-portion fixed region in which the leak-proof cuff is fixed so as not to stand up;
in the end-portion fixed region of one or both of the front portion and the rear portion, the outwardly-folded portion is fixed by a partially joined region, in which joined portions are dispersedly arranged, to a lower member located on the lower surface side of the outwardly-folded portion;
the elastic member provided to the outwardly-folded portion has, at an end portion in the longitudinal direction, a free end portion whose stretched state has been released; and
the free end portion is arranged in a manner overlapping a non-joined portion within the partially joined region in the outwardly-folded portion.

{21}
The disposable diaper as set forth in any one of clauses {1} to {20}, wherein:
the leak-proof cuff includes, in each of the front portion and the rear portion, an end-portion fixed region in which the leak-proof cuff is fixed so as not to stand up;
in the end-portion fixed region of one or both of the front portion and the rear portion, the outwardly-folded portion is fixed by a partially joined region, in which joined portions are dispersedly arranged, to a lower member located on the lower surface side of the outwardly-folded portion; and
the partially joined region includes the joined portions and non-joined portions alternately in one direction in a planar view of the outwardly-folded portion and in a direction orthogonal to the one direction.

{22}
The disposable diaper as set forth in any one of clauses {1} to {21}, wherein:
the outwardly-folded portion includes a lateral extension portion that extends more toward the outer side, in the width direction, than the lateral side edge of the absorbent core; and
in the front portion or the rear portion, the lateral extension portion is joined to a lower member located on the lower surface side of the outwardly-folded portion in an area occupying from 2 to 30% of an area of an opposition region in which the outwardly-folded portion opposes the lower member.

{23}
The disposable diaper as set forth in any one of clauses {1} to {22}, wherein the outwardly-folded portion is not joined to the inwardly-oriented portion opposing the outwardly-folded portion.

{24}

The disposable diaper as set forth in any one of clauses {1} to {23}, wherein:

the leak-proof-cuff-forming sheet material is a multilayer-structure laminate sheet including a two-layer structure formed by folding a single sheet in two along a folding/bending portion formed at the free end of the leak-proof cuff; and the elastic members are fixed by an adhesive between the layers of the laminate sheet.

{25}

The disposable diaper as set forth in any one of clauses {1} to {24}, wherein, in the leak-proof cuff, no elastic member is provided along the longitudinal direction in either the inwardly-oriented portion or the fold-back portion.

{26}

The disposable diaper as set forth in any one of clauses {1} to {25}, wherein the outwardly-folded portion's length L1 in the width direction is preferably 1.1 times or greater, more preferably 1.5 times or greater, and preferably 5 times or less, more preferably 3 times or less, the inwardly-oriented portion's length L2 in the width direction.

{27}

The disposable diaper as set forth in any one of clauses {1} to {26}, wherein the outwardly-folded portion's length L1 in the width direction is preferably 10 mm or greater, more preferably 15 mm or greater, and preferably 50 mm or less, more preferably 40 mm or less.

{28}

The disposable diaper as set forth in any one of clauses {1} to {27}, wherein the inwardly-oriented portion's length L2 in the width direction is preferably 5 mm or greater, more preferably 8 mm or greater, and preferably 45 mm or less, more preferably 35 mm or less.

{29}

The disposable diaper as set forth in any one of clauses {1} to {28}, wherein the length L3, in the width direction, of an elastic region, in which the elastic members in the outwardly-folded portion are provided, to the outwardly-folded portion's length L1 in the width direction is preferably 15% or greater, more preferably 30% or greater, and preferably 80% or less, more preferably 65% or less.

{30}

The disposable diaper as set forth in any one of clauses {1} to {29}, wherein the length L3, in the width direction, of the elastic region, in which the elastic members in the outwardly-folded portion are provided, is preferably 3 mm or greater, more preferably 6 mm or greater, and preferably 25 mm or less, more preferably 20 mm or less.

{31}

The disposable diaper as set forth in any one of clauses {1} to {30}, wherein:

the outwardly-folded portion includes a lateral extension portion that extends more toward the outer side, in the width direction, than the lateral side edge of the absorbent core; and the length L4, in the width direction, of the leak-proof cuff's lateral extension portion to the outwardly-folded portion's length L1 in the width direction is preferably 15% or greater, more preferably 35% or greater, and preferably 85% or less, more preferably 65% or less.

{32}

The disposable diaper as set forth in any one of clauses {1} to {31}, wherein:

the outwardly-folded portion includes a lateral extension portion that extends more toward the outer side, in the width direction, than the lateral side edge of the absorbent core; and the lateral extension portion's length L4 in the width direction is preferably 3 mm or greater, more preferably 6 mm or greater, and preferably 30 mm or less, more preferably 25 mm or less.

{33}

The disposable diaper as set forth in any one of clauses {1} to {32}, wherein the elongation stress at 70% elongation of the inner region is preferably 1.2 times or greater, more preferably 2 times or greater, and preferably 5 times or less, more preferably 4 times or less, the elongation stress at 70% elongation of the outer region.

{34}

The disposable diaper as set forth in any one of clauses {1} to {33}, wherein the elongation stress at 70% elongation of the inner region is preferably 0.25 N or greater, more preferably 0.3 N or greater, and preferably 1.5 N or less, more preferably 1.0 N or less.

{35}

The disposable diaper as set forth in any one of clauses {1} to {34}, wherein the elongation stress at 70% elongation of the outer region is preferably 0.05 N or greater, more preferably 0.15 N or greater, and preferably 1.0 N or less, more preferably 0.5 N or less.

{36}

The disposable diaper as set forth in any one of clauses {1} to {35}, wherein the length Lc of the elastic member closest to the free end side, among the plurality of elastic members, to the length La of the elastic member closest to the fold-back portion is preferably 70% or greater, more preferably 80% or greater, and preferably 95% or less, more preferably 90% or less.

{37}

The disposable diaper as set forth in any one of clauses {1} to {36}, wherein:

the outwardly-folded portion includes a lateral extension portion that extends more toward the outer side, in the width direction, than the lateral side edge of the absorbent core; and in one or both of the front portion and the rear portion, the lateral extension portion is joined to a lower member located on the lower surface side of the outwardly-folded portion in an area occupying preferably from 2 to 30%, more preferably from 5 to 25%, of the area of an opposition region in which the outwardly-folded portion opposes the lower member.

{38}

The disposable diaper as set forth in any one of clauses {1} to {37}, wherein:

the disposable diaper comprises second leak-proof cuffs each including a second leak-proof-cuff-forming sheet material and a second elastic member fixed in a stretched state to the sheet material along the longitudinal direction, the second leak-proof cuffs being respectively provided widthwisely outside of the leak-proof cuffs that are provided respectively to the absorbent assembly's both lateral sides along the longitudinal direction; and a length of the second leak-proof cuff from the lateral side edge of the absorbent core to the second elastic member is longer than the total length of a length of the inwardly-oriented portion of the leak-proof cuff and a length from the fold-back portion to the elastic member provided to the outwardly-folded portion.

{39}

The disposable diaper as set forth in any one of clauses {1} to {38}, wherein:

the disposable diaper comprises second leak-proof cuffs each including a second leak-proof-cuff-forming sheet material and second elastic members fixed in a stretched state to the sheet material along the longitudinal direction, the second leak-proof cuffs being respectively provided widthwisely outside of the leak-proof cuffs that are provided respectively to the absorbent assembly's both lateral sides along the longitudinal direction; and an elastic region in which the plurality of second elastic members are provided in the second leak-proof cuff has a higher elongation stress at 70% elongation than the outer region of the leak-proof cuff.

{40}

The disposable diaper as set forth in any one of clauses {1} to {39}, wherein:

the disposable diaper comprises second leak-proof cuffs each including a second leak-proof-cuff-forming sheet material and a second elastic member fixed in a stretched state to the sheet material along the longitudinal direction, the second leak-proof cuffs being respectively provided widthwisely outside of the leak-proof cuffs that are provided respectively to the absorbent assembly's both lateral sides along the longitudinal direction; and the length L5 from the absorbent core's lateral side edge to the second elastic member is preferably 105% or greater, more preferably 110% or greater, and preferably 180% or less, more preferably 150% or less, and preferably from 105 to 180%, with respect to the total length of the inwardly-oriented portion's length L2 in the width direction and the length L6 from the fold-back portion to the elastic member provided to the outwardly-folded portion.

{41}

The disposable diaper as set forth in any one of clauses {1} to {40}, wherein:

the disposable diaper comprises second leak-proof cuffs each including a second leak-proof-cuff-forming sheet material and a second elastic member fixed in a stretched state to the sheet material along the longitudinal direction, the second leak-proof cuffs being respectively provided widthwisely outside of the leak-proof cuffs that are provided respectively to the absorbent assembly's both lateral sides along the longitudinal direction; and the length L5 from the absorbent core's lateral side edge to the second elastic member is preferably 15 mm or greater, more preferably 20 mm or greater, and preferably 50 mm or less, more preferably 40 mm or less.

{42}

The disposable diaper as set forth in any one of clauses {1} to {41}, wherein:

the disposable diaper comprises second leak-proof cuffs each including a second leak-proof-cuff-forming sheet material and a second elastic member fixed in a stretched state to the sheet material along the longitudinal direction, the second leak-proof cuffs being respectively provided widthwisely outside of the leak-proof cuffs that are provided respectively to the absorbent assembly's both lateral sides along the longitudinal direction; and the total length of the inwardly-oriented portion's length L2 in the width direction and the length L5 from the absorbent core's lateral side edge to the second elastic member is preferably 10 mm or greater, more preferably 15 mm or greater, and preferably 45 mm or less, more preferably 30 mm or less.

{43}

The disposable diaper as set forth in any one of clauses {1} to {42}, wherein:

the disposable diaper comprises second leak-proof cuffs each including a second leak-proof-cuff-forming sheet material and second elastic members fixed in a stretched state to the sheet material along the longitudinal direction, the second leak-proof cuffs being respectively provided widthwisely outside of the leak-proof cuffs that are provided respectively to the absorbent assembly's both lateral sides along the longitudinal direction; and the elongation stress of the elastic region in which the second elastic members are provided in the second leak-proof cuff is preferably 0.2 N or greater, more preferably 0.3 N or greater, and preferably 1.5 N or less, more preferably 1.0 N or less.

{44}

The disposable diaper as set forth in any one of clauses {1} to {43}, wherein:

the disposable diaper comprises second leak-proof cuffs each including a second leak-proof-cuff-forming sheet material and second elastic members fixed in a stretched state to the sheet material along the longitudinal direction, the second leak-proof cuffs being respectively provided widthwisely outside of the leak-proof cuffs that are provided respectively to the absorbent assembly's both lateral sides along the longitudinal direction; and the elongation stress at 70% elongation of the elastic region in which the second elastic members are provided in the second leak-proof cuff and the elongation stress at 70% elongation of the inner region of the leak-proof cuff are substantially the same, or the elongation stress at 70% elongation of the inner region of the leak-proof cuff is greater.

{45}

The disposable diaper as set forth in any one of clauses {1} to {44}, wherein the leak-proof cuff includes a water-impervious layer between two layers of nonwoven fabric.

{46}

The disposable diaper as set forth in any one of clauses {1} to {45}, wherein the sheet material forming the leak-proof cuff is a spunbond-meltblown-spunbond laminate nonwoven fabric including a nonwoven fabric having a bulk softness value of 7 cN or less.

{47}

The disposable diaper as set forth in any one of clauses {1} to {46}, wherein:

the outer cover is divided into the front portion and the rear portion; and the absorbent assembly is fixed in a manner bridging a front panel located in the front portion and a rear panel located in the rear portion.

INDUSTRIAL APPLICABILITY

With the disposable diaper of the present invention, it is possible to easily achieve both reduction in the width of the crotch portion and widening of the hydrophilic width. Also, when putting the diaper on the wearer, the wearer's foot is prevented from getting caught on the first leak-proof cuff or the peripheral edge portion around the leg opening, thus allowing the diaper to be worn smoothly and also allowing the wearer to move his/her legs easily during use.

An additional effect is that leakage is less likely to occur. Furthermore, the inner region—which is located on the inner side, in the width direction, of the first leak-proof cuff's outwardly-folded portion—can easily come into contact with the wearer's inguinal region, whereas the outer region—which is located on the outer side in the width direction—can easily come into contact with and conform to the skin surface of the wearer's inner femoral region, thereby suppressing the formation of a gap between the first leak-proof cuff and the wearer's skin. It is also possible to reduce the burden of bringing the first leak-proof cuff into contact with the skin surface.

The invention claimed is:

1. A disposable diaper having a longitudinal direction along a front-rear direction of a wearer and a width direction orthogonal to the longitudinal direction, the disposable diaper including a rear portion to be arranged on the wearer's rear side when worn, a front portion to be arranged on the wearer's front side and a crotch portion located between the rear portion and the front portion, the disposable diaper comprising:
an absorbent assembly including a topsheet, a backsheet and an absorbent member that is interposed between the topsheet and the backsheet and that includes an absorbent core; and
a pair of leak-proof cuffs provided respectively to the absorbent assembly's both lateral sides along the longitudinal direction, wherein:
each of the leak-proof cuffs includes a leak-proof-cuff-forming sheet material and elastic members fixed to the sheet material, and includes
an inwardly-oriented portion wherein the sheet material is arranged from a lateral side edge of the absorbent core toward the absorbent member's inner side in the width direction,
a fold-back portion where the sheet material is folded back toward the absorbent member's outer side in the width direction, the fold-back portion being located above the absorbent member, and
an outwardly-folded portion ranging from the fold-back portion to a free end of the leak-proof cuff;
the outwardly-folded portion has a length, in the width direction, that is longer than the length of the inwardly-oriented portion;
the plurality of elastic members are fixed in a stretched state to the outwardly-folded portion along the longitudinal direction;
the free end of the leak-proof cuff is located widthwisely outside of the lateral side edge of the absorbent core; and
in the outwardly-folded portion, in a case where a region where the plurality of elastic members are provided is divided, in the outwardly-folded portion's width direction, into two equal parts defined respectively as an inner region and an outer region, the inner region has a higher elongation stress at 70% elongation than the outer region.

2. The disposable diaper according to claim 1, wherein, as regards the elastic members provided to the outwardly-folded portion, the number of elastic members, in the width direction, arranged more toward the free end side than the position of the lateral side edge of the absorbent core is greater than the number of elastic members arranged more toward the fold-back portion side than the position of the lateral side edge of the absorbent core.

3. The disposable diaper according to claim 1, wherein, among the elastic members provided to the outwardly-folded portion, the closer the elastic member is to the free end, the smaller the fineness thereof.

4. The disposable diaper according to claim 1, wherein, among the elastic members provided to the outwardly-folded portion, the closer the elastic member is to the free end, the smaller the elongation rate thereof.

5. The disposable diaper according to claim 1, wherein:
three or more elastic members are provided to the outwardly-folded portion; and
a spacing between the elastic members adjacent to one another in the width direction is the same for all of the elastic members, or becomes longer the closer the elastic members are to the free end.

6. The disposable diaper according to claim 1, wherein all of the elastic members provided to the outwardly-folded portion are provided more toward the free end side than the position of the lateral side edge of the absorbent core, including the position of the lateral side edge.

7. The disposable diaper according to claim 1, wherein, among the elastic members provided to the outwardly-folded portion, the elastic member located closest to the fold-back portion overlaps the position of the lateral side edge of the absorbent core in the width direction.

8. The disposable diaper according to claim 1, wherein, among the elastic members, the closer the elastic member is to the free end, the shorter the length, along the longitudinal direction, of a range in which the elastic member is fixed in a stretched state.

9. The disposable diaper according to claim 1, wherein:
the leak-proof cuff includes, in each of the front portion and the rear portion, an end-portion fixed region in which the leak-proof cuff is fixed so as not to stand up;
the outwardly-folded portion includes a lateral extension portion that extends more toward the outer side, in the width direction, than the lateral side edge of the absorbent core; and
in the end-portion fixed region of one or both of the front portion and the rear portion, the lateral extension portion is fixed by a partially joined region, in which joined portions are dispersedly arranged, to a lower member located on a lower surface side of the lateral extension portion.

10. The disposable diaper according to claim 1, wherein:
the leak-proof cuff includes, in each of the front portion and the rear portion, an end-portion fixed region in which the leak-proof cuff is fixed so as not to stand up;
in the end-portion fixed region of one or both of the front portion and the rear portion, the outwardly-folded portion is joined by a first joined portion to a lower member located on a lower surface side of the outwardly-folded portion; and
in the outwardly-folded portion, an area of the first joined portion is larger on the outer side in the width direction than on the inner side.

11. The disposable diaper according to claim 1, wherein:
the leak-proof cuff includes, in each of the front portion and the rear portion, an end-portion fixed region in which the leak-proof cuff is fixed so as not to stand up;
in the end-portion fixed region of one or both of the front portion and the rear portion, the inwardly-oriented portion is joined by a second joined portion to a lower member located on a lower surface side of the inwardly-oriented portion; and
in the inwardly-oriented portion, an area of the second joined portion is larger on the inner side in the width direction than on the outer side.

12. The disposable diaper according to claim 1, wherein:
the leak-proof cuff includes, in each of the front portion and the rear portion, an end-portion fixed region in which the leak-proof cuff is fixed so as not to stand up;

in the end-portion fixed region of one or both of the front portion and the rear portion, the outwardly-folded portion is joined by a first joined portion to a lower member located on the lower surface side of the outwardly-folded portion, and the inwardly-oriented portion is joined by a second joined portion to the topsheet located on the lower surface side of the inwardly-oriented portion; and an area of the first joined portion is smaller than an area of the second joined portion.

13. The disposable diaper according to claim 12, wherein:

a cover nonwoven fabric that covers a skin-facing surface side of the absorbent assembly is provided to an end portion, in the longitudinal direction, of the absorbent assembly in one or both of the front portion and the rear portion;

the outwardly-folded portion of the leak-proof cuff is joined by a third joined portion to the cover nonwoven fabric; and the area of each of the first joined portion and the second joined portion is larger than an area of the third joined portion.

14. The disposable diaper according to claim 1, wherein:

the leak-proof cuff includes, in each of the front portion and the rear portion, an end-portion fixed region in which the leak-proof cuff is fixed so as not to stand up;

in the end-portion fixed region of one or both of the front portion and the rear portion, the outwardly-folded portion is fixed by a partially joined region, in which joined portions are dispersedly arranged, to a lower member located on the lower surface side of the outwardly-folded portion;

the elastic member provided to the outwardly-folded portion has, at an end portion in the longitudinal direction, a free end portion whose stretched state has been released; and the free end portion is arranged in a manner overlapping a non-joined portion within the partially joined region in the outwardly-folded portion.

15. The disposable diaper according to claim 1, wherein:

the outwardly-folded portion includes a lateral extension portion that extends more toward the outer side, in the width direction, than the lateral side edge of the absorbent core; and in the front portion or the rear portion, the lateral extension portion is joined to a lower member located on the lower surface side of the outwardly-folded portion in an area occupying from 2 to 30% of an area of an opposition region in which the outwardly-folded portion opposes the lower member.

16. The disposable diaper according to claim 1, wherein the outwardly-folded portion is not joined to the inwardly-oriented portion opposing the outwardly-folded portion.

17. The disposable diaper according to claim 1, wherein:

the disposable diaper comprises second leak-proof cuffs each including a second leak-proof-cuff-forming sheet material and a second elastic member fixed in a stretched state to the sheet material along the longitudinal direction, the second leak-proof cuffs being respectively provided widthwisely outside of the leak-proof cuffs that are provided respectively to the absorbent assembly's both lateral sides along the longitudinal direction; and a length of the second leak-proof cuff from the lateral side edge of the absorbent core to the second elastic member is longer than a total length of a length of the inwardly-oriented portion of the leak-proof cuff and a length from the fold-back portion to the elastic member provided to the outwardly-folded portion.

18. The disposable diaper according to claim 1, wherein:

the disposable diaper comprises second leak-proof cuffs each including a second leak-proof-cuff-forming sheet material and second elastic members fixed in a stretched state to the sheet material along the longitudinal direction, the second leak-proof cuffs being respectively provided widthwisely outside of the leak-proof cuffs that are provided respectively to the absorbent assembly's both lateral sides along the longitudinal direction; and an elastic region in which the plurality of second elastic members are provided in the second leak-proof cuff has a higher elongation stress at 70% elongation than the outer region of the leak-proof cuff.

19. The disposable diaper according to claim 1, wherein the leak-proof cuff includes a water-impervious layer between two layers of nonwoven fabric.

20. The disposable diaper according to claim 1, wherein the sheet material forming the leak-proof cuff is a spunbond-meltblown-spunbond laminate nonwoven fabric including a nonwoven fabric having a bulk softness value of 7 cN or less.

* * * * *